(12) United States Patent
Gray et al.

(10) Patent No.: US 6,183,966 B1
(45) Date of Patent: *Feb. 6, 2001

(54) APPARATUS AND METHOD FOR SELECTIVELY RANKING SEQUENCES FOR ANTISENSE TARGETING

(75) Inventors: Donald M. Gray, Richardson; Christopher L. Clark, Plano, both of TX (US)

(73) Assignee: Board of Regents, University of Texas System, Dallas, TX (US)

(*) Notice: Under 35 U.S.C. 154(b), the term of this patent shall be extended for 0 days.

This patent is subject to a terminal disclaimer.

(21) Appl. No.: 09/235,614

(22) Filed: Jan. 22, 1999

Related U.S. Application Data

(63) Continuation of application No. 08/808,474, filed on Mar. 3, 1997, now Pat. No. 5,856,103, which is a continuation of application No. 08/320,507, filed on Oct. 7, 1994, now abandoned.

(51) Int. Cl.[7] .................................................. C12Q 1/68
(52) U.S. Cl. ................................................................ 435/6
(58) Field of Search ........................ 435/6, 5; 536/23.1; 514/44

(56) References Cited

PUBLICATIONS

Agrawal, S. et al *Proc. Natl. Acad. Sci. U.S.A.*, 85:7079–7083, 1988.
Agrawal, S. et al *Proc. Natl. Acad. Sci. U.S.A.*, 86:7790–7794, 1989.
Bennett, C.F. et al., Inhibition of Endothelial Adhesion Molecule Expression with Antisense Oligonucleotides, *J. of Immunology*, 152:3530–3540, 1994.
Bernstein, P., "Start Making Antisense," Research Brief in *Nature Biotechnology* 16:10 (1998).
Buck, H.M., et al., *Science*, 248:208–212, 1990.
Cantor, C.R., et al., "Biophysical Chemistry Part III," W.H., San Francisco, pp. 1187–1190, 1980.
Cavenave, C., et al., *Nucl. Acids Res.*, 17:4255–4273, 1989.
Cohen, J.S., "Oligonucleotides–Antisense Inhibitors of Gene Expression," CRC Press, Boca Rotan, FL, 1989.
Cory, D.R. and Schultz, P.G., *Science*, 238:1401–1403, 1987.
Eckstein, F., *Anal Bioichem.* 54:367–402, 1985.
Freier, S.M., et al., *Thermodynamics of Antisense Oligonucleoide Hybridization* in "Gene Regulation: Biology of Antisense RNA and DNA" (Eds. Erickson, R.P. & Izant, J.G.) pp. 95–107, Raven Press, Ltd., New York, 1992.
Goldstein, R.F. and Benight, A.S., "How Many Numbers are Required to Specify–Sequence Dependent Properties of Polynucleotides?" *Biopolymers*, 32:1679–1693, 1992.
Goodchild, S., et al., *Proc. Natl. Acad. Sci. U.S.A.*, 859:5507–5511, 1988.

Gray, D.M., "Derivation of nearest–neighbor properties from data on nucleic acid oligomers. I. Simple sets of independent sequences and the influence of absent nearest neighbors," *Biopolymers*, 42:783–793, 1997a.
Gray, D.M., "Derivation of nearest–neighbor properties from data on nucleic acid oligomers. II. Thermodynamic parameters of DNA•RNA hybrids and DNA duplexes," *Biopolymers*, 42:795–810, 1997b.
Gray, D.M. and Tinoco, Jr., I., "A New Approach to the Study of Sequence–Dependent Properties of Polynucleotides," *Biopolymers*, 9:223–244, 1970.
Gray, G.D., et al., *Biochem. Pharmacol.* 53:1465–1476, 1997.
Hashem, G.M., et al. "Hybrid Oligomer Duplexes Fored with Phosphorothroate DNAs: CD Spectra and Melting Temperatures of S–DNA:RNA Hybrids are Sequence–Dependent but Consistent with Similar Heteronomous Conformations," *Biochemistry*, 37:61–72, 1998.
Hung, S.H., et al., "Evidence from CD Spectra that d(purine): r(pyrimidine) and r(purine): (pyrimidine) Hybrids are in Different Structural Classes," *Nucl. Acids. Res.*, 22:4326–4334, 1994.
Kiessling, L.L., et al., "Flanking Sequence Effects within the Pyrimidine Triple–Helix Motif Characterized by Affinity Clearing," *Biochemistry*, 31:2829–2834.
Laughton, D.A., and Neidle, S., "Prediction of the Structure of the Y+:R–:R+ Type DNA Triple Helix by Molecular Modeling," *Nucl. Acids. Res.*, 20:6535–6541, 1992.
Lesnik, E.A. and Freier, S.M., "Relative Thermodynamic Stability of DNA, RNA, and DNA:RNA Hybrid Duplexes: Relationship with Base Composition and Structure," *Biochemistry*, 35:10807–10815, 1995.
Letsinger, R.L., et al., *Proc. Natl. Acad. Sci. U.S.A.*, 86:6553–6556, 1989.
Lisziewicz, J., et al., "Antisense Oligodeoxynucleotide Phosphorothioate Complementary to Gag mRNA Blocks Replication of Human Immunodeficiency Virus Type I in Human Peripheral Blood Cells," *Proc. Natl. Acad. Sci. U.S.A.*, 91:7942–7946, 1994.

(List continued on next page.)

*Primary Examiner*—Scott W. Houtteman
(74) *Attorney, Agent, or Firm*—Locke Liddell & Sapp LLP

(57) ABSTRACT

The invention provides methods of identifying a nucleic acid molecule having a sequence capable of targeting a gene of interest, and hence nucleic acid molecules useful in gene theraphy and disease treatment. A system and method for selecting antisense DNA oligonucleotide sequences that will form the most stable DNA:RNA hybrids within a given target mRNA sequence is provided. An apparatus capable of identifying a subject nucleic acid sequence capable of targeting a gene of interest is further provided. The apparatus includes the use of a software program and a computing unit. Methods for controlling gene expression are also provided.

40 Claims, 4 Drawing Sheets

PUBLICATIONS

Marcus–Sekura, C.J., *Anal. Biochem*, 172:289–295, 1988.
Matsukura, M., et al., *Proc. Natl. Acad. Sci. U.S.A.*, 84:7706–7710, 1987.
Matsukura, M., et al., *Gene*, 72:343–347, 1988.
Melton, D.A. (Ed.) "Antisense RNA and DNA," Cold Spring Harbor Press, Cold Spring Harbor, 1988.
Mercola, D. and Cohen, J.S., *Cancer Gene Therapy*, 2:47–59, 1995.
Mori, K., et al., *Nucl. Acids Res.*, 17:8207–8219, 1989.
Pilch, D.S., et al., "Structure, Stability and Thermodynamics of a Short Intermolcular Purine–Purine–Pyrimidine Triple Helix," *Biochemistry*, 30:6081–6087, 1991.
Press, W.H., et al., "Numerical Recipes in C, the Art of Scientific Computing," $2^{nd}$ edition, (pp. 59–70, Cambridge University Press, Cambridge, England), 1992.
Ratmeyer, L., et al., "Sequence Specific Thermodynamic and Structural Properties for DNA:RNA duplexes," *Biochemistry*, 33:5298–5304, 1994.
Sarin, P.S., et al., *Proc. Natl. Adac. Sci. U.S.A.*, 85:7448–7451, 1988.
Shibahara, S., et al., *Nucl. Acids. Res.*, 17:239–252, 1989.
Stein, C.A. and Chen, Y.–C., "Antisense Oligonucleotides as Therapeutic Agents—Is the Bullet Really Magical?" *Science*, 261:1004–1012, 1993.

Stein, C.A., and Cohen, J.S., "Oligodeoxynucleotides as Inhibitors of Gene Expression; A Review," *Cancer Research*, 48:2659–2668, 1988.
Stevenson, M., and Iversen, P.L., *J. Gen Virol.*, 70:2673–2682, 1989.
Stull, R.A., et al., "Predicting Antisense Oligonucleotide Inhibitory Efficacy: A Computational Approach Using Histograms and Thermodynamic Indices," *Nucl. Acids Res.*, 20:3501–3508, 1992.
Sugimoto, N., et al., "Thermodynamic Parameters to Predict Stability of RNA/DNA Hybrid Duplexes," *Biochemistry*, 34:11211–11216, 1995.
Toulmé, J. –J. and Hélène, C., "Antimessenger Oligodeoxynucleotides: An Alternative to Antisense RNA for Artificial Regulation of Gene Expression—A Review," *Gene*, 72:51–58, 1988.
Ven der Krol, A.R., et al., *BioTechniques*, 6:958–973, 1988.
Walder, J., *Genes & Development*, 2:502–504, 1988.
Walder, R.T. and Walder, J.A., *Proc. Natl. Acad. Sci U.S.A.*, 85:5011–5015, 1988.
Zaia, J.A. et al., *J. Virol*, 62:3914, 1988.
Zamecnik, P. et al., *Proc. Natl. Acad. Sci. U.S.A.*, 83:4143–4146, 1986.
Zamecnik, P. and Stephenson, M., *Proc. Natl. Acad. Sci U.S.A.*, 75:280–284, 1978.

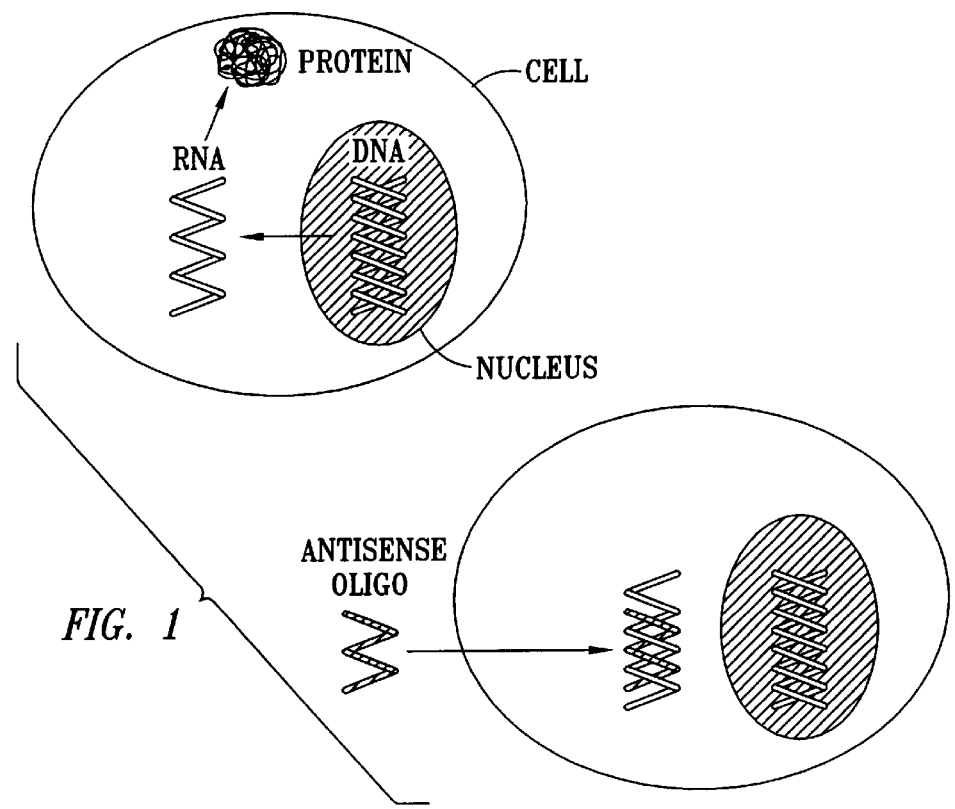
FIG. 1
FIG. 2
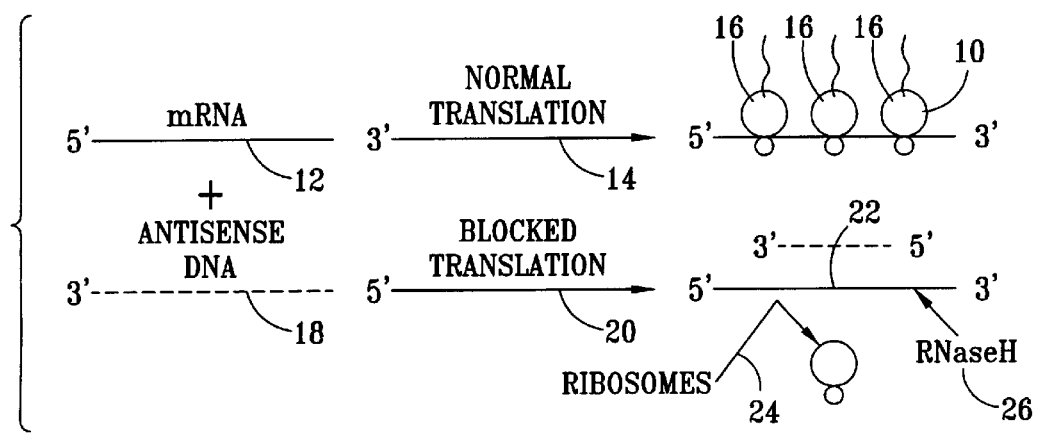

APPARATUS AND METHOD FOR SELECTIVELY RANKING SEQUENCES FOR ANTISENSE TARGETING

This application is a continuing application of Ser. No. 08/808,474, filed Mar. 3, 1997, now U.S. Pat. No. 5,856,103 which is a continuing application of Ser. No. 08/320,507 filed Oct. 7, 1994 now abandoned.

TECHNICAL FIELD

The present invention generally relates to an apparatus and method for ranking nucleic acid sequences based on stability of nucleic acid oligomer sequence binding interactions to select sequence zones for antisense targeting.

BACKGROUND OF THE INVENTION

Bodily states in mammals, including disease states, are at least in part directly affected by proteins. Those proteins, acting directly or through enzymatic functions, contribute in large proportion to many diseases in animals and humans. In the past, therapeutic treatment has focused on interactions with those proteins in an effort to moderate the disease. Attempts have also been made to moderate the actual production of such proteins by interaction with molecules that directly affect their synthesis, i.e., the DNA sequence that underlies the gene product. It is well known that by interfering with the production of the proteins, the effect of the therapeutic results can be maximized. Likewise, therapeutic approaches have been developed that interfere with gene expression, leading to undesired formations which need to be patrolled. There are numerous methods that have been formulated for inhibiting specific gene expression which have been adopted to some degree and have been defined as antisense nucleic acids. The basic approach is that an oligonucleotide analog complimentary to a specific targeted messenger RNA or mRNA sequence is used. Pertinent references include those of Stein and Cohen (1988); Walder (1988); Marcus-Sekura (1988); Zon (1988); Van der Krol (1988) and Matteucci and Wagner (1996). Each of the foregoing concern general antisense theory and prior techniques.

Background of Antisense Technology

The term "antisense" generally connotes an approach to chemotherapy which is based upon the complementary pairing of an antisense oligonucleotide, or ASO, with a target nucleic acid. The use of an ASO compound requires a complementarity of the antisense base sequence to a target zone of an mRNA, so that the ASO will bind to that mRNA target sequence and will bring about selective inhibition of gene expression (D. A. Melton, 1988; Stein and Cohen, 1988; and Toulmé and HéllIne, 1988). A more thorough understanding of such technology can be found in a book edited by Cohen (Oligonucleotides—*Antisense Inhibitors of Gene Expression* (1989)), and a recent review by Mercola and Cohen (1995).

Referring to FIG. 1, the schematic representation of the process of transfer of information from the DNA genome to a protein product can be seen. If the gene product (protein) is one whose controlled synthesis is essential for the well-being of the organism or cell, then a defective synthesis or an unwanted protein can lead to illness or death. FIG. 1 also illustrates that an antisense oligonucleotide (or oligo) can be used to inhibit or terminate protein synthesis.

A summary of the relevant portion of the disclosure from the review by Cohen (Id., 1989, pp. 1–6) is set forth below. There are five basic assumptions included in this approach:

(1) Cellular uptake: It is assumed that the oligo will cross the cell membrane and will be able to reach its target sequence within the cell.
(2) Stability: The oligo will be stable under in vivo conditions, and will reach the target sequence in significant quantity.
(3) Hybridization: The oligo will hybridize with the target sequence so that a DNA:RNA hybrid will be produced.
(4) Inhibition of expression: The formation of this hybrid will prevent the expression of the gene(s) coded for by the hybridized mRNA.
(5) Selectivity of binding: The oligo will not be bound non-selectively to many other sites, particularly protein sites so as to have its effective concentration, or potency reduced.

The results of early studies that showed selective inhibition of gene expression in Rous sarcoma virus with a synthetic 13-mer (Zamenik and Stephenson, 1978) indicated that this oligo was indeed penetrating into cells. However, the general resistance to this possibility, and the difficulty in synthesizing oligos of such length until the mid-1980's, slowed progress in this area.

Once automated oligo synthesis became possible, further attempts were made to test this antisense approach. It has now been established that antisense oligonucleotides can be actively taken up by cells and can accumulate in the cellular nucleus (G. D. Gray et al., 1997).

Initial attempts to inhibit gene expression naturally concentrated on normal oligos with phosphodiester linkages. However, it has been believed that since these compounds are known to be subject to enzymatic hydrolysis by nucleases in vivo and in vitro, they could not form the basis of an effective antisense strategy. This problem of low oligo stability could explain the high concentrations of oligos that were found to be required to bring about inhibition of expression in some of the early work. Further, the breakdown of an informational molecule in which the integrity of the base sequence is integral to its mode of action would obviously be a devastating restriction on the strategy of the antisense approach.

Any chemical modification in an oligo can lead to a change in hybridization with its target mRNA sequence at physiological temperature. Since the object of this strategy is to ensure that hybridization occurs, it is mandatory that the hydrogen bonding capability of the bases not be impaired. It is for this reason that the modifications that are made in the oligo are usually in the backbone, and not in the bases or the sugars. Nevertheless, there are many possible modifications of the three portions of the nucleotide unit, only a few of which have so far been investigated. However, in order not to disrupt the formation of Watson-Crick base pairing, it is preferable that any modification that is made should be rather conservative. For example, the substitution of one sulfur atom for any oxygen or phosphate is perhaps the most conservative substitution that can be envisaged that accomplishes the aim of nuclease stability (Eckstein, 1985) without significantly impairing the hybridization of the oligo. The prospect for hybridization of an oligo with a mRNA must also take account of the fact that RNAs can have complex folded tertiary structures and, thus, the target sequence should be contained within a single-stranded accessible region.

The mechanics of inhibition of gene expression were originally presumed to arise from interference of the hybrid DNA:RNA duplex with ribosomal processing. This mechanism has been termed translation arrest or hybridization arrest. However, subsequent work has shown that ribonucleases that hydrolyze such hybrids, namely RNase-H, are actively involved in the mechanism of action (Walder and Walder, 1988). This was shown very clearly by comparison of normal oligos which have the beta configuration of the base-sugar linkage, and non-natural alpha-oligos, which form hybrids with RNA that are not susceptible to RNase-H, and which were concomitantly found not to produce translational arrest (Cavenave et al., 1989). The most potent antisense effects are obtained when RNA translation is blocked by RNase-H cleavage (Matteucci and Wagner, 1996).

It is important for the effectiveness of the antisense oligo approach that the oligo bind selectively to the target complementary sequence. If the oligo is bound non-selectively to the other sites, particularly protein sites that are present in the cell, the potency of any oligo as a putative drug would be severely limited. Eckstein has shown in a series of elegant studies (Eckstein, 1985) that phosphorothioate oligos have a tendency to bind to protein sites and to inhibit nucleases. This "problem" can, in fact, be turned into an advantage if the oligos interact specifically with a protein site, and thus inhibit, for example, a process that is required for vital proliferation. This has been found to be the case with the phosphorothioate analogues which inhibit certain polymerases in a sequence non-specific manner. Such an inhibition cannot be described as an antisense effect. However, the inhibition of HIV reverse transcriptase by phosphorothioate antisense oligomers (S-ASOs) (Matsukura et al.; 1987; 1988), and the effectiveness of ASOs have led to twelve clinical trials (Mercola and Cohen, 1995; Matteucci and Wagner, 1996) illustrating that phosphorothioates are particularly valuable. This is largely because phosphorothioates retain the ability to activate RNase-H.

If RNA is to be regarded as the legitimate target for this novel class of drugs, then much can be done to improve their effectiveness. One of the chief questions that arises is what part of the mRNA to target, for example one might target the 5' initiation codon as one of the preferred sites.

The covalent addition of intercalative or reactive groups onto either the 3' or 5' end of the oligo is already established as an appropriate modification of the antisense approach. In the former case, the intercalator is intended to enhance oligo binding, thus enabling short oligos to be used more effectively. While this would reduce the cost of an oligo, this tactic involves relatively non-selective interaction compared to a longer, more selective antisense base sequence. Alkylating agents attached to oligos have been used for chemical modifications of the other strand in a DNA duplex, but can also be adapted for DNA:RNA duplexes. The whole area of attaching hydrolyzing groups to the oligo (Stein and Cohen, 1988) or even ribonucleases (Corey and Schultz, 1987), is still very much in its infancy, although the cellular uptake and antigenicity of such putative oligo-enzymes is clearly a problem that must be addressed.

Referring to FIG. 2, a system for translation of mRNA is illustrated. More specifically, an mRNA polymer sequence 12 generally is acted on by ribosome machinery 10 such that if normal translation 14 occurs then nascent polypeptides 16 will readily be formed to give a sequence of amino acids. Conversely, if the mRNA binds an antisense DNA oligomer (ASO) sequence 18, a blocked translation 20 occurs, either because ribosomes 24 cannot translate or because RNase-H 26 cleaves at the hybrid sequence 22.

The antisense oligomer is generally DNA, instead of RNA, since RNase-H only attacks the RNA strand of DNA:RNA hybrids. Many chemical modifications of the antisense oligomer are possible, such as the substitution of phosphates in the sugar-phosphate linkages with phosphorothioate linkages. Set forth below is an illustration of the unmodified phosphate linkage and the phosphorothioate linkage.

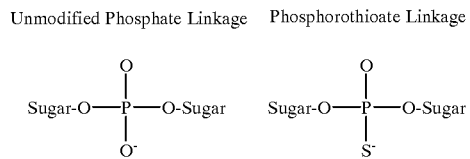

Prior attempts to inhibit HIV gene synthesis by various antisense approaches have been made by a number of researchers. Zamecnik and coworkers have used a transcriptase primer site and splice donor/acceptor sites (P. C. Zamecnik et al., 1986). Goodchild and coworkers have made phosphodiester compounds targeted to the initiation sites for translation, the cap site, the polyadenylation signal, the 5' repeat region and a site between the gag and pol genes (J. Goodchild et al., 1988). In the Goodchild study, the greatest activity was achieved by targeting the polyadenylation signal. Agrawal and coworkers have extended the studies of Goodchild by using chemically modified oligonucleotide analogs, which were also targeted to the cap and splice donor/acceptor sites (S. Agrawal et al., 1988). Agrawal and coworkers have used oligonucleotide analogs targeted to the splice donor/acceptor site to inhibit HIV infection in early infected and chronically infected cells (S. Agrawal et al., 1989).

Sarin and coworkers have also used chemically modified oligonucleotide analogs targeted to the cap and splice donor/acceptor sites (P. S. Sarin et al., 1988). Zaia and coworkers, on the other hand, used an oligonucleotide analog targeted to a splice acceptor site to inhibit HIV (J. A. Zaia et al., 1988). Matsukura and coworkers synthesized oligonucleotide analogs targeted to the initiation of translation of the rev gene mRNA (M. Matsukura et al., 1987). Mori and coworkers used a different oligonucleotide analog targeted to the same region as targeted by Matsukura (K. Mori et al., 1989). Shibahara and coworkers used oligonucleotide analogs targeted to a splice acceptor site as well as to the reverse transcriptase primer binding site (S. Shibahara et al., 1989). Letsinger and coworkers synthesized and tested oligonucleotide analogs with conjugated cholesterol targeted to a splice site (Letsinger et al., 1989). Stevenson and Iversen conjugated polylysine to oligonucleotide analogs targeted to the splice donor and the 5' end of the first exon of the tat gene (Stevenson and Iversen, 1989). Buck and coworkers have recently described the use of phosphate-methylated DNA oligonucleotides targeted to HIV mRNA and DNA (H. M. Buck et al., 1990). In addition, a U.S. Patent issued to Ecker, has disclosed the use of synthetic oligonucleotides to inhibit the activity of the HIV virus (U.S. Pat. No. 5,166,195).

The need has, therefore, arisen for a systematic method and apparatus for identifying target DNA and RNA sequences in a predictable, logical pattern. Also required is a process that optimizes a ranking of nucleic acid sequences for targeting with antisense oligonucleotides. In addition, there is a long felt need for a means of assessing the thermodynamics and strength of nucleic acid hybridization in sequences that are to be the targets of antisense gene targeting technology in order to efficiently and expeditiously affect their expression. In *Nature Biotechnology*, Bernstein recently wrote, referring to antisense molecules, "the first step in their design—target identification—continues to be a major bottleneck" (Bernstein, 1998).

SUMMARY OF THE INVENTION

In antisense technology, a synthesized nucleic acid oligomer sequence is bound to a mRNA polymer sequence by the pairing of bases, such as by using A, G, C or T for the DNA sequence of bases to target mRNA sequences containing U, C, G or A, respectively. Such pairing results in a duplex helical nucleic acid that is a DNA:RNA double-stranded hybrid containing one deoxyribonucleic acid (DNA) strand and one ribonucleic acid (RNA) strand. Since the paired hybrids can affect various cellular processes, such as the translation of an mRNA message into a protein, this invention discloses a method and an apparatus for selectively ranking an antisense oligonucleotide (ASO) to increase the efficiency of the antisense process and to more cost effectively engineer oligonucleotides for targeting specific genetic structures.

In one aspect, the invention comprises a data processing system for identifying nucleic acid sequences for antisense oligonucleotide targeting. More specifically, the system comprises a control computer that is coupled to a memory system which has, within one portion of the memory system, the value data list for combinations of nearest-neighbor nucleic acid pair. Such data list is a list of values for independent combinations of nearest-neighbor nucleic acid pairs. This data list is determined by referring to a set of predetermined experimental values for known nucleic acid sequences. In practice, a data list of values of thermodynamic energies needed for splitting combinations of nearest-neighbor base pairs apart is used to determine the ranking and, thus, the priority of sequences for antisense pairing. Therefore, without ever assigning values of thermodynamic parameters or melting temperatures to individual nearest-neighbors, the thermodynamic data acquired for combinations of oligomeric or polymeric DNA:RNA hybrid sequences can be used to predict the values of other oligomeric or polymeric DNA:RNA hybrid combinations of nearest-neighbors. The control computer also obtains, via user input, from a memory system or via modem transfer, a nucleic acid sequence that is to be analyzed for target sequences. The term "target sequence", as used herein, refers to a nucleic acid segment that is being targeted for antisense oligonucleotide antigene treatment of cells.

Having obtained the sequence to be analyzed and the data list of values for combinations of nearest-neighbor nucleic acid pairs, a program is executed by the control computer. The program contains computer instructions which perform a comparison of said value data list for nearest-neighbor nucleic acid pair combinations and said nucleic acid sequence. A unique feature of the execution of the program of the present invention is that it operates by using combinations of nearest-neighbor base pair stabilities, rather than relying on assignments of the individual nearest-neighbor base pair stabilities. It is not generally understood in the field that the thermodynamic data acquired for an array of polymeric or oligomeric sequences are restricted such that thermodynamic values for individual nearest-neighbors simply cannot be extracted and assigned without making a number of assumptions about their interactions.

For polymeric sequences, there are three restrictions on the combinations of any nearest-neighbor value that can be expressed in an equation in terms of the nearest-neighbors listed in Table 2, hereinbelow, where N is the number of occurrences of that nearest-neighbor combination in a sequence, as derived by Gray & Tinoco (1970), and the number in the parenthesis is the numerical values of the nearest-neighbor assigned in Table 2, below. The first equation expresses the fact that the number of times an rU:dA pair comes before another type of base pair must equal the number of times it comes after another type of base pair. Equations can be similarly written for rA:dT, rC:dG, and rG:dC base pairs to give a total of four equations.

1. Restriction on rU:dA base pair:
   $N(1)+N(2)+N(3)+N(4) \quad N(2)+N(6)+N(10)+N(14)$.
2. Restriction on rA:dT base pair:
   $N(5)+N(6)+N(7)+N(8)=N(1)+N(5)+N(9)+N(13)$.
3. Restriction on rC:dG base pair:
   $N(9)+N(10)+N(11)+N(12)=N(3)+N(7)+N(11)+N(15)$.
4. Restriction on rG:dC base pair:
   $N(13)+N(14)+N(15)+N(16)=N(4)+N(8)+N(12)+N(16)$.

Since one of the four equations can be derived from the other three, only three are independent restrictions. The apparatus and method of the present invention maintain these restrictions throughout the comparison of target sequences.

The apparatus and method of the present invention relies on, and uses, data for polymeric sequences. In the case of oligomeric sequences that vary in length, for example those of less than 20 nucleotides in length, there are five total constraints on the possible combinations of nearest-neighbors. Again, these constraints make it impossible to assign thermodynamic parameters to individual nearest-neighbors (see below). The present invention can also use data from such shorter oligomeric sequences, where end effects are important. Therefore, it is possible, with sufficient data to predict the stabilities of DNA:RNA hybrid sequences of any length.

In another aspect, the invention is a method for selectively ranking sequences for antisense targeting. The method, which employs a control computer comprises the steps of:

determining the fraction of each type of nearest-neighbor base pair in each target RNA:ASO-DNA hybrid sequence;

substituting the nearest-neighbor base pair fraction into formulas to determine the fraction of each of the thirteen (13) polymers within contiguous segments of the target nucleic acid sequence;

multiplying the fractions times the values of hybridization temperature (or thermodynamic energy) for the polymers to create a stability ranking and yield the relative hybridization temperatures for potential antisense oligonucleotides; and ranking the different nucleic acid segments for which relative hybridization strength has been determined according to hybridization potential, wherein the formulas used to identify the highest and lowest hybridization temperatures (or thermodynamic energies) along the length of the target nucleic acid sequence are a summation of the hybridization temperatures (or thermodynamic energies) as they relate to the relative base pairings. Alternatively, the nucleic acid segments can be ranked by other parameters, such as C+G content.

When dealing with antigene technology, the antigene oligomer binds to a double-stranded DNA sequence. Although different types of nearest-neighbor base pairs can exist, which create a secondary consideration when assessing the location of binding, the principle that only combinations of nearest-neighbors can be used to predict binding energies is exactly the same as for the prediction of antisense DNA binding energies. Thus, in another aspect the invention is a method and system for selectively ranking DNA sequences for antigene targeting.

In yet another aspect, the present invention is a method of operating a control computer for compiling a list of ranked nucleic acid sequences which method comprises the steps of:

provideing a program and its identifier in a portion of a memory unit of the control computer;

obtaining a nucleic acid sequence; obtaining a data list of values for combinations of nearest-neighbor nucleic acid pairs;

obtaining a user-defined nucleic acid segment length value;

determining the length of the DNA segment to be analyzed according to the nucleic acid segment length value used; and comparing the target nucleic acid sequence to the data list of values based on the user-defined nucleic acid segment length and calculating a nearest-neighbor value for each overlapping and contiguous length of the target nucleic acid sequence of said user-defined nucleic acid segment length to obtain a hybridization value for each segment having the user-defined length. The target sequence is analyzed in a concatenated fashion in all possible reading frames as shown for example in Table 1 below.

In still another aspect, the present invention is a nearest-neighbor comparison compiler stored on a storage medium comprising:

a first set of binary code for obtaining a nucleic acid sequence in a first data format;

a second set of binary code for comparing the nucleic acid sequence and the data list of values for combinations of nearest-neighbor nucleic acid pairs; and a third set of binary code for electronically routing the binary values to an output device.

One example of these sets of binary code is the Nearest-Neighbor Thermal Stability Program (NNTSA).

The present invention, in yet another aspect, is a computer-implemented method of determining the relative hybridization potential of nucleic acid segments comprising:

reading a nucleic acid sequence on a storage medium;

obtaining a user-defined nucleic acid sequence segment length;

separating the nucleic acid sequence into overlapping nucleic acid segments based on the user-defined nucleic acid sequence segment length;

comparing the nucleic acid sequence that has been separated into nucleic acid segments to a data list of values for combinations of nearest-neighbor nucleic acid pairs; and determining a hybridization potential or ranking for each nucleic acid segment from the set of binary data. This computer-implemented process for determining the relative hybridization potential can be used to obtain a list that ranks hybridization potential based on the nearest-neighbor determination in a given, e.g. descending order.

Available Programs to Compare with NNTSA

There are a number of programs available that can be used to calculate thermodynamic values for pairing two nucleic acid sequences. A chief purpose of these programs is the calculation of melting temperatures or stabilities of short primer DNA strands bound to longer template DNA strands, where the primer DNA strands are intended to be elongated by the polymerase chain reaction (PCR). Other purposes of common programs are for choosing hybridization probes. Probe oligomers are used to bind to desired gene sequences that have been separated (for example, by gel electrophoresis) from a mixture of sequences or to identify which bacterial clones, or other hosts of cloned vectors, carry the specified gene sequences. For these reasons, the thermodynamic data used by other programs are, in general, the data for hybridization of two DNA or of two RNA strands.

Some examples of such methods and programs known to the inventor are the Stull et al. method to calculate Dscore, the OLIGO program by Molecular Insights, Inc., and the HYBsimulator program by Advanced Gene Computing Technologies, Inc.

The NNTSA program is different from the above programs in that its fundamental purpose is to calculate the melting temperatures or other stability ranking values for hybrids formed from one DNA strand and one RNA strand. The data needed are different for DNA:RNA duplexes and for DNA:DNA or RNA:RNA duplexes, for the reasons set forth on pp. 22–23, following Table 2, of the Specifications. Different data are needed to calculate the stabilities of DNA:RNA hybrids than are needed to calculate the stabilities of either DNA:DNA or RNA:RNA duplexes, since both strands are the same in the latter duplexes.

A direct comparison of results with our method and results with the Stull et al. program is given as EXAMPLE 1.

The HYBsimulator used in the present invention makes use of Sugimoto et al. (1995) to calculate stabilities of DNA:RNA hybrids. To the inventor's knowledge, it is the only program that currently does so.

The NNTSA program of the present invention uses a different methodology from that used by any other program known to the inventor to calculate stabilities. The methodology involves the inclusion of constraints in the calculations of nearest-neighbor properties. The constraints for long DNA:RNA hybrid sequences are given in pp. 24–25 of the Specifications and are repeated in relevant claims. The NNTSA program can be expanded to be used for triple-stranded sequences as in EXAMPLE 5 of the Specifications and for short hybrid duplex sequences as in EXAMPLE 6 of the Specifications where constraints are specified in Table 17.

Because of the new methodology on which the NNTSA program is based, which involves a set number of constraints as given in theoretical papers by Gray (1997a, 1997b), the number of data entries can be fixed at the minimum number for the most accurate analyses. Thirteen combinations of nearest-neighbor parameters as given in Tables 4 and 7 are used by the NNTSA program to calculate the stabilities of hybrid sequences that are relatively long (e.g. 20 base pairs long). The HYBsimulator program uses 17 parameters to calculate stabilities of hybrids regardless of the number of base pairs in the sequence.

Finally, data for a set of 13 independent sequence combinations of phosphorothioate S-DNA oligomers hybridized with RNA can only be used by the program described herein, since this set of data is sufficient to provide the minimal number of 13 parameters, as specifically given in Tables 5 and 7. However, the program can also make use of the Sugimoto et al. data set for unmodified DNA:RNA hybrids and other data sets for DNA:DNA or RNA:RNA duplexes.

BRIEF DESCRIPTION OF THE DRAWINGS

The present invention can be more readily understood by reference to the detailed description, taken in conjunction with the accompanying drawings of which:

FIG. 1 is an illustration of a system for the synthesis of RNA sequences from DNA, and protein from RNA, and the point of antisense DNA:RNA hybridization;

FIG. 2 is a more detailed illustration of blocked protein synthesis using an antisense oligomer.

Figure 3:
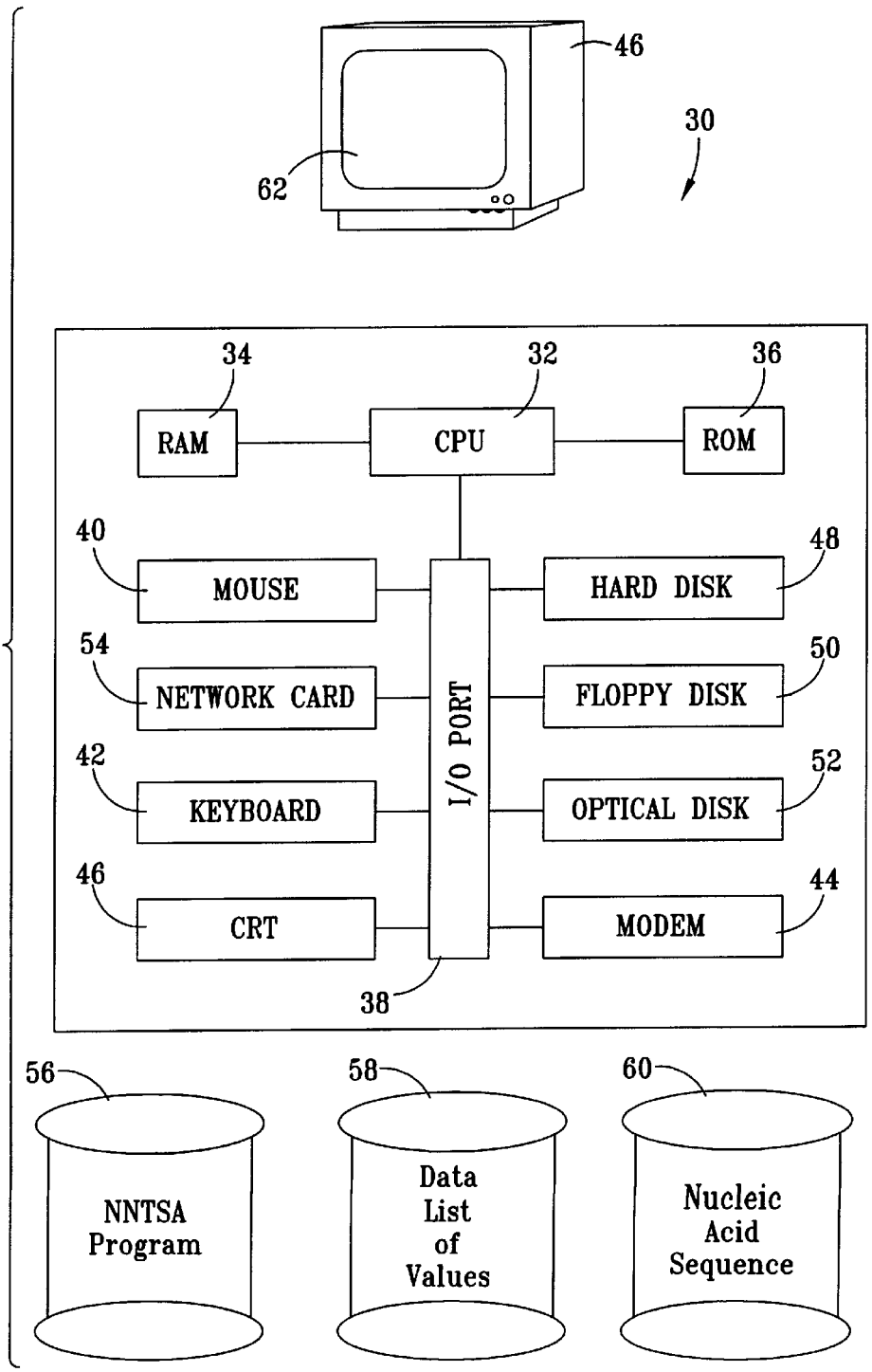
FIG. 3 is a schematic view of the control computer system of the present invention and is comprised of the following components.
Figure 4:
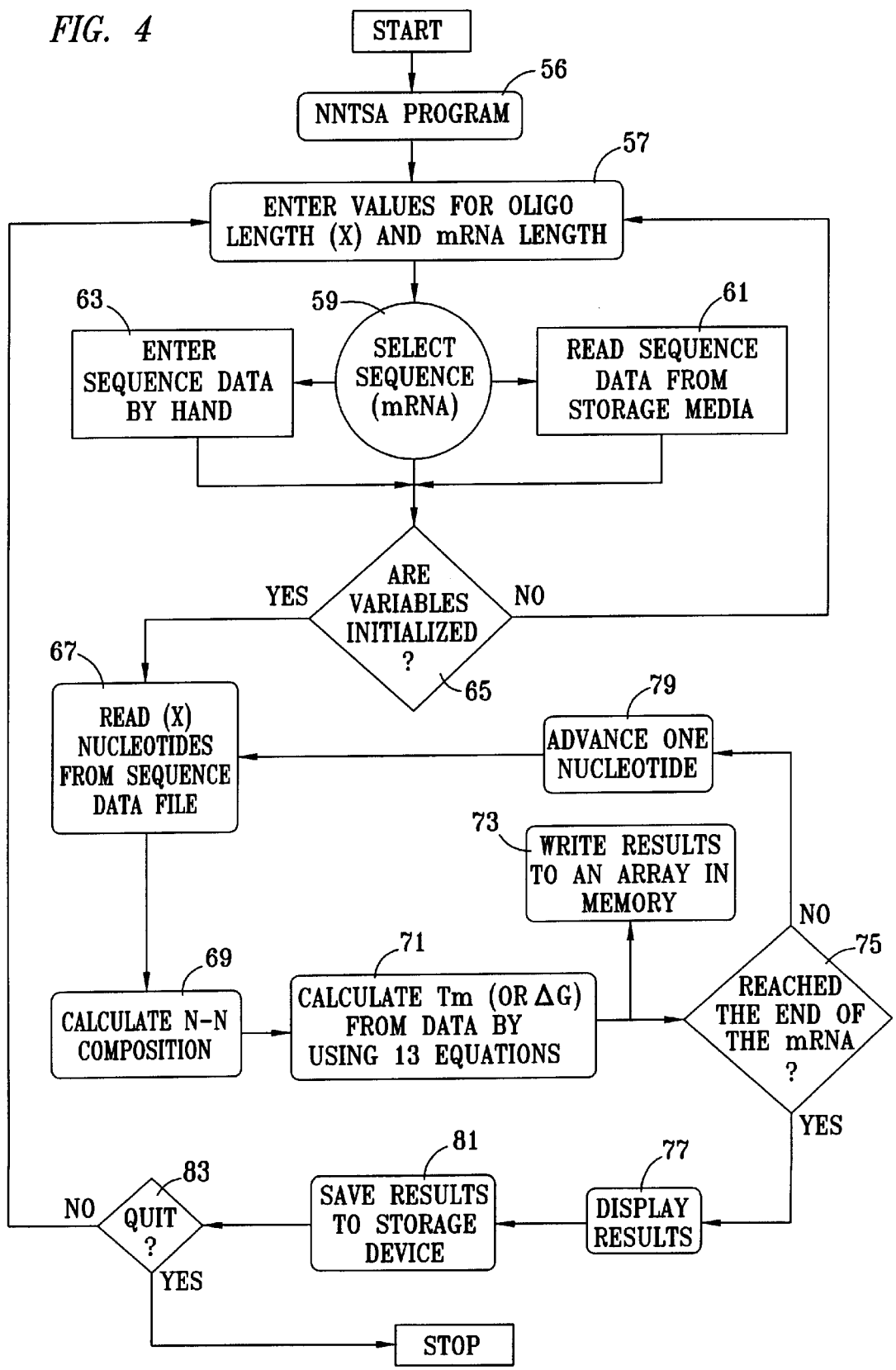
Figure 5:
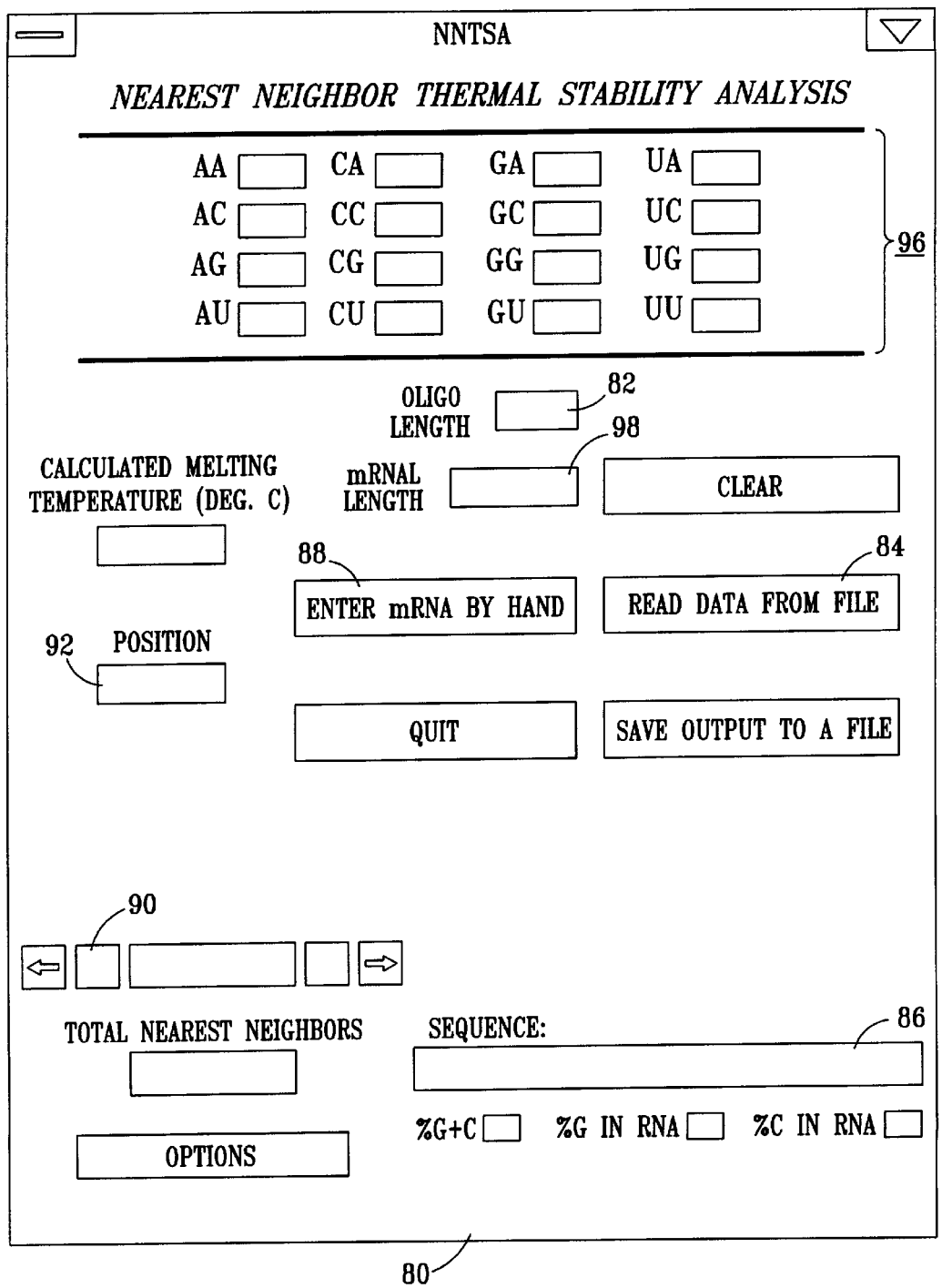

32: CPU
34: RAM
36: ROM
38: I/O port
40: mouse
42: keyboard
44: modem
46: CRT
48: hard disk
50: floppy disk
52: optical disk
54: network card
56: NNTSA program
58: Data List of Values
60: Nucleic Acid Sequence
62: monitor;

FIG. 4 represents the various parts of a logic flow diagram showing the overall operation of the present invention; and FIG. 5 illustrates a typical nearest-neighbor display screen generated by the system of the present invention.

Corresponding numerals and symbols in the different figures refer to corresponding parts unless otherwise indicated.

DETAILED DESCRIPTION OF THE PREFERRED EMBODIMENTS

The present invention employs an antisense DNA technology wherein DNA oligomer sequences that bind to mRNA polymer sequences by pairing of the bases (A, G, C, or T) of the DNA sequence with the bases (U, C, G, or A, respectively) of the mRNA sequence. Such pairing results in a duplex helical nucleic acid that is a DNA:RNA double-stranded hybrid, containing one deoxyribonucleic acid (DNA) strand and one ribonucleic acid strand (RNA). The paired bases then affect various cellular processes, such as the prevention of translation of the mRNA message into a protein. While not intended to be limited to any particular theory or mechanism, the prevention of mRNA translation can be by physical blockage of the ribosomes or by other mechanisms such as the degradation of the RNA transcript by RNase-H at the site of DNA binding.

To more readily understand the meaning and scope of the present invention, set forth below are some definitions:

DEFINITIONS

ASO and AGO—antisense oligomer (ASO) and antigene oligomer (AGO)

S-ASO—antisense oligomer with phosphorothioate linkages.

Target nucleic acid—molecule of mRNA, of duplex DNA, or of another nucleic acid, the control of which is desired. Such molecules can have 100's or 1000's or more nucleotides or base pair subunits in a linear array.

Sequence—the order of the nucleotides, which generally comprise A, U, G and C for mRNA, and A, T, C and G for DNA or the order of base pairs, which can comprise A:T and G:C for duplex DNA, within a linear target nucleic acid.

n-mer target sequence—the number of nucleotide or base pair subunits in the entire target nucleic acid, n, is typically more than 20 and can be larger than 1000.

Target zone—a subsequence within a target nucleic acid. The target zone will typically be about 20 nucleotides long in an mRNA or 20 base pairs long in a duplex DNA.

m-mer target sequence zone—target sequence zone that consists of a subsequence of m nucleotides in a mRNA or m base pairs within the target DNA duplex. In particular embodiments, m is about 20. There are n−m+1 target sequence zones within an n-mer target sequence.

Each interior m-mer zone overlaps at least one nucleotide or base pair with 2 (m−1) other m-mer zones within the target mRNA or duplex DNA.

m-mer ASO—a sequence that is complementary to an m-mer target sequence zone within an mRNA. For nucleic acid sequences, the base complementarity is typically as follows: A, T, G and C of the ASO pairs with U, A, C and G of the target sequence zone. The ASO can be of any type of normal or modified nucleic acid or peptide or other chemical molecule that has a defined complementarity to the n-mer target sequence zone.

n-mer AGO—a sequence that is complementary to an m-mer target sequence zone within a duplex DNA. The base complementarity rules depend on the type of triplex that forms. The AGO can be of any type of normal or modified nucleic acid or peptide or other chemical molecule that has a complementarity to the n-mer target sequence zone.

Rank of m-mer target sequence zones or rank of m-mer ASOs or rank of m-mer AGO's—the thermodynamic stability rank is the αG Gibb's free energy, or an approximation to the αG, for the reaction "target m-mer zone" + "m-mer ASO or AGO" <-> "complex of zone:ASO or zone:AGO," and is the rank of the complex of an m-mer target sequence zone paired together with its complementary m-mer ASO or complementary m-mer AGO sequence. The rank is higher for a more stable complex, i.e., more negative ΔG.

Independent model m-mer sequences—A minimum set of sequences, defined as in Gray and Tinoco (1970) or Gray (1997a), whose stability ranks can be used to determine the stability ranks of all possible m-mer target sequence zones and whose stability ranks are referred to herein as the data list of values for combinations of nearest-neighbor nucleic acid pairs.

Computer Control Apparatus and System

Referring now to FIG. 3, there is shown one embodiment of a control computer based system 30 of the present invention for identifying nucleic acid sequences for antisense oligonucleotide targeting. The control computer 30 can be a personal computer comprised of CPU 32, RAM 34, ROM 36 and Input/Output ports 38. Additional peripheral units such as mouse 40, keyboard 42 and modem 44 can be connected to I/O ports 38. A CRT 46 can be used to display information generated by control computer 30 which can also include hard disk 48, floppy disk 50, and optical disk 52. Control computer 30 can also be connected to a computer network via network card 54 or modem 44.

As previously mentioned, a software program, such as, for example, the Nearest-Neighbor Thermal Stability Analysis (NNTSA) program, will be used in the method of the invention.

The NNTSA program 56 is operated by control computer 30 and can be stored in memory on hard drive 48, floppy disk 50, optical disk 52, or any other memory storage medium. A data list of values for combinations of nucleic acid nearest-neighbor pairs 58 can be accessed by control computer 30 while control computer 30 is operating NNTSA program 56. The data list of values for combinations of nucleic acid nearest neighbor pairs 58 can be stored in the memory of control computer 30 on hard drive 48, floppy disk 50, optical disk 52 or any other memory storage medium or can be remotely accessed via modem 44 or network card 54. The data list of values 58 includes the values assigned to thirteen (13) combinations of the sixteen possible nearest-neighbor pairs, which provide for hybridization strength values based on Tm or ΔG° values and the nearest-neighbor effect, as described hereinbelow in Table 7 for S-DNA:RNA phosphorothioate backbone nucleic acid hybrids. The nucleic acid sequence 60 which is to be analyzed by the NNTSA program 56 can be input into control computer 30 via keyboard 42, can be remotely accessed via network card 54 or modem 44 or can be stored in hard drive 48, floppy disk 50, optical disk 52 or any other memory storage medium.

Examples of storage media that can be used with the present invention include, but are not limited to: magnetic tape, optical disk, compact disk, hard disk, floppy disk, ferroelectric memory, optical storage, electrically erasable programmable read only memory (EEPROM), flash memory, read only memory (ROM), static random access memory (SRAM), dynamic random access memory (DRAM), ferromagnetic memory, charge coupled devices, smart cards, and like storage media.

FIG. 4 is a logic flow diagram of the NNTSA program 56. In step 57, the NNTSA program 56 prompts the user to enter parameters for both the length of the oligonucleotide (default is 24) and the length of the messenger RNA (mRNA) to scan. The length of the mRNA to scan can range from a minimum length equal to that of the oligonucleotide to a maximum length equal to the total length of the mRNA (up to 4000 bases). After both of these parameters have been entered, the NNTSA program 56 can proceed to the next step 59 where the mRNA sequence on which to perform an analysis is selected. This sequence can either be read in from a memory storage medium in step 61 or entered by the user in a text window in step 63. The NNTSA program 56 then checks to see if the initial parameters for oligonucleotide length and mRNA length have been entered and are valid in step 65. If the result is "Yes" or "True", the NNTSA program 56 proceeds to step 67. If the result is "No" or "False", the NNTSA program returns to step 57 at which time reentry of the data or corrected data can be requested.

In step 67, the NNTSA program 56 reads into the memory X number of nucleotides of the mRNA sequence where X is equal to the number of nucleotides specified for the oligonucleotide length in step 57. In step 69, the NNTSA program 56 calculates the nearest-neighbor composition of the sequence of nucleotides just previously read. The result is a tally for each of the 16 possible nearest-neighbor base pairs (NN$_1$=A, NN$_2$=B, NN$_3$=C, etc.). The NNTSA program 56 then substitutes these values into the appropriate nearest-neighbor equations in combination with the data list of values for combinations of nearest-neighbor pairs 58 to determine the relative stability (either Tm or ΔG° depending on the data set used) of the sequence in step 71. In step 73, the results of the calculation can be stored in an array in the memory with each successive result occupying a separate position in the array. In step 75, the NNTSA program 56 checks to see if the end of the mRNA sequence has been reached. If the result is "Yes" or "True", the NNTSA program 56 proceeds to step 77. If the result is "No" or "False", the program proceeds to step 79.

If the end of the mRNA sequence has not been reached, the NNTSA program 56 increments one nucleotide further down the mRNA sequence, increments the position mark by one unit and returns to step 67. Once the end of the mRNA sequence has been reached, the results of all calculations are routed to an output device, such as CRT 46. In step 81, the user can save the results to a memory storage medium such as hard disk 48 or floppy disk 50. In step 83, the user can select the quit button in which case the NNTSA program 56 is ended. Otherwise, the user is free to execute the program multiple times as necessary by returning to step 57.

As stated, the output from the analysis described in FIG. 4 can be viewed on screen 62 by scanning through the nucleic acid sequence, or can be viewed via a computer print-out. Other means of analyzing the values can be through further computer manipulations. These manipulations can include, for example, viewing the list of values based on nucleic acid content or increasing or decreasing hybridization rank value. The hybridization rank values assigned to each segment can also be transferred to another dynamic or permanent storage medium before or after analysis.

FIG. 5 depicts a graphical user interface, such as screen 80, which can be used by the present invention to request information for a nucleic acid nearest-neighbor analysis. Screen 80 comprises an oligo length user defined input window 82 and a READ DATA FROM FILE button 84, that permits the user to browse through, for example a disk drive, hard drive or network, for a nucleic acid sequence. Once acquired and processed, the nucleic acid sequence appears in sequence window 86. Alternatively, the nucleic acid sequence can be input by hand by pressing the ENTER MRNA BY HAND button 88. The nucleic acid sequence is then input by hand via a keyboard or any other input device. Using scroll bar 90, the relative position of the nearest-neighbor segment analysis is displayed in position window 92, which conforms with the sequence displayed in the sequence window after processing is complete. The individual count of each nearest-neighbor pair per oligo length segment is displayed in each of the nearest-neighbor pair boxes 96. Also, the operator-specified length of the mRNA is displayed in mRNA length window 98. Another output available for display from the screen is the total number of nearest-neighbors that is in the segment length being displayed in sequence window 86.

Practical Uses of the Apparatus

A DNA oligonucleotide of more than about 17 nucleotides in length would have a unique sequence relative to the entire human genome, as set forth in the article by Stein and Chen (1993). mRNAs are each much longer, 100's to 1000's of nucleotides long, and provide many overlapping target sites for binding of an antisense DNA oligomer (ASO). Table 1 below illustrates a short segment of a theoretical mRNA sequence to which many ASOs ten nucleotides long (10-mers) can be targeted.

TABLE 1

Illustration of Overlapping Subtarget Sequences mRNA: (SEQ ID NO: 1)
5'-A-C-G-G-G-C-C-U-C-U-C-U-U-G-C-A-A-G-G-G-C-U-A-A-G-G-U-3'

TABLE 1-continued

Illustration of Overlapping Subtarget Sequences

Possible overlapping 10-mer ASOs that could form base pairs with the mRNA starting at the 5' end of the mRNA:
3' T-G-C-C-C-G-G-A-G-A 5'

(SEQ ID NOS 2-7, respectively)

G-C-C-C-G-G-A-G-A-G

C-C-C-G-G-A-G-A-G-A

C-C-G-G-A-G-A-G-A-A

C-G-G-A-G-A-G-A-A-C

G-G-A-G-A-G-A-A-C-G etc.

For an mRNA that is n nucleotides long, there are n−m+1 different sequences (sites) to which m-mer ASOs can bind. Thus, according to the above description, the present method and apparatus will provide the artisan the relative stabilities of each possible ASO hybridized to its "target sequence zone" sequence and thereby directing the artisan to synthesize only those which will be most stable. Such optimization assures that only the most stable ASOs are tested as potential drugs, or as inhibitors of gene expression, and thereby further creating a more expeditious and efficient process for targeting these compounds.

The thermodynamic stability of an ASO, i.e., the equilibrium constant that determines the proportion of ASOs of a given sequence that are bound to a target site, is a function of the structure of a given neighboring hybrid base pair, with the assumption that there are no intrastrand mRNA or intrastrand ASO complexes that compete with the binding in a sequence-specific manner. Any such considerations that might affect the availability or the concentration of the target sequence zone can be added as secondary considerations. The primary consideration is the relative merit of different sequence sites for binding ASOs where the mRNAs and ASOs are not involved in competing complexes (self-complexes or complexes with other cellular components that bind specific sequences). There are 16 DNA:RNA hybrid nearest-neighbor base pairs, which are shown in Table 2, that must be considered.

TABLE 2

16 Nearest-Neighbor Base Pairs in DNA:RNA Hybrids

| 1 | r(U-A)<br>d(A-T) | 2 | r(U-U)<br>d(A-A) | 3 | r(U-C)<br>d(A-G) | 4 | r(U-G)<br>d(A-C) |
|---|---|---|---|---|---|---|---|
| 5 | r(A-A)<br>d(T-T) | 6 | r(A-U)<br>d(T-A) | 7 | r(A-C)<br>d(T-G) | 8 | r(A-G)<br>d(T-C) |
| 9 | r(C-A)<br>d(G-T) | 10 | r(C-U)<br>d(G-A) | 11 | r(C-C)<br>d(G-G) | 12 | r(C-G)<br>d(G-C) |

TABLE 2-continued

16 Nearest-Neighbor Base Pairs in DNA:RNA Hybrids

| 13 | r(G-A)<br>d(C-T) | 14 | r(G-U)<br>d(C-A) | 15 | r(G-C)<br>d(C-G) | 16 | r(G-G)<br>d(C-C) |
|---|---|---|---|---|---|---|---|

The RNA sequence is on the top and DNA is on the bottom. The strand directions are 5'-3' on the top and 3'-5' on the bottom.

There is a need to solve the problem of determining the relative contributions of each of these nearest-neighbor base pairs to the stability of a hybrid formed by an ASO sequence. Contributions of these individual nearest-neighbors generally cannot be separated as parts of complex nucleic acid sequences. They always appear in combinations whose properties can be determined. The apparatus and method of the present invention which employs scientific theory and experimental data can: (a) determine the minimum number of RNA:DNA sequence combinations whose properties need to be determined; and (b) select the ASO sequence that will form the most stable hybrid among all those possible in a given target mRNA sequence, given that the mRNA target sequences are in equivalent states (i.e. not complexed, or identically complexed).

The nearest-neighbor base pairs are usually combined in a sequence. The only exceptions are the four sequences formed from homopolymers: r(U-U):d(A-A), r(A-A):d(T-T), r(C-C):d(G-G), r(G-G): d(C-C). Each of these four nearest-neighbors can exist as the sole type of nearest-neighbor in a sequence. Whenever more than one type of base is in each strand, there is a combination of nearest-neighbors. For example, the hybrid sequence $r(A-G)_{12}$:d(C-T)$_{12}$ has 12 nearest-neighbors of the type r(A-G):d(C-T) and 11 of the type r(G-A):d(T-C). All of the purines (A and G) are in the RNA strand and all of the pyrimidines (C and T) are in the DNA strand (SEQ ID NOS 8–9, respectively):

```
                1  2  3  4  5  6  7  8  9  10 11 12
mRNA: 5' A-G-A-G-A-G-A-G-A-G-A-G-A-G-A-G-A-G-A-G-A-G-A-G 3'

DNA:  3' T-C-T-C-T-C-T-C-T-C-T-C-T-C-T-C-T-C-T-C-T-C 5'
                1  2  3  4  5  6  7  8  9  10 11
```

Also, the above hybrid sequence is chemically different from the one below, which has the purines (A and G) in the DNA strand and the pyrimidines C and U in the RNA strand (SEQ ID NOS 10–11, respectively):

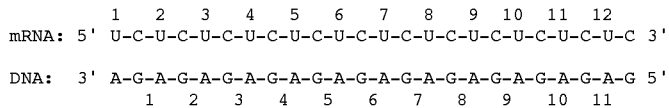

This oligomer duplex has 12 nearest-neighbors of the type r(U-C):d(G-A) and 11 of the type r(C-U):d(A-G).

As shown in Table 3, the two oligomer duplexes diagramed above are of different stabilities. Table 3 gives the data for the melting temperatures (Tm values) of 16 oligomer duplexes, including oligomers containing alternating AG:CT (or AG:CU) base pairs. The DNA:DNA duplex has a Tm of 59.4 degrees. In comparison, the RNA:RNA duplex has a Tm of 69.5 degrees. These Tm values are different, and the Tm of a hybrid is not necessarily the average of these two values. The hybrid that has the purines bases A and G on the RNA strand has a Tm of 64.0 degrees while the hybrid that has the purine bases in the DNA strand is much less stable, with a Tm of 43.2 degrees. The same pattern holds for the other three sets of oligomer duplexes.

The hybrid duplexes are different in stability from duplexes of the DNA:DNA or RNA:RNA type, where both strands have the same sugar-phosphate backbone. In addition, the stability of hybrids cannot be determined by the simple (G+C)-content, since both of the hybrids in this example have 50% G:C base pairs and 50% A:T (or A:U) base pairs.

TABLE 3

Duplex Melting Temperatures and Tm Values

|  | Tm(deg C.) |
|---|---|
| DNA:DNA Duplex | |
| d(AG):d(CT) | 59.4 ± 0.5 |
| d(AGG):d(CCT) | 63.4 ± 0.5 |
| d(AAG):d(CTT) | 50.0 ± 0.05 |
| d(AAGG):d(CCTT) | 57.9 ± 0.0 |
| r(AG):r(CU) | 69.5 ± 1.0 |
| r(AGG):r(CCU) | 77.6 ± 0.3 |
| r(AAG):r(CUU) | 53.5 ± 1.5 |
| r(AAGG):r(CCUU) | 70.9 ± 0.0 |
| DNA:DNA Hybrid | |
| d(AG):r(CU) | 43.2 ± 0.8 |
| d(AGG):r(CCU) | 46.2 ± 0.8 |
| d(AAG):r(CUU) | 33.4 ± 1.4 |
| d(AAGG):r(CCUU) | 47.4 ± 0.5 |
| r(AG):d(CT) | 64.0 ± 0.9 |
| r(AGG):d(CCT) | 69.4 ± 0.5 |
| r(AAG):d(CTT) | 51.6 ± 1.2 |
| r(AAGG):d(CCTT) | 66.4 ± 0.5 |

All sequences were 24 base pairs long. The buffer was 0.05M sodium phosphate, pH 7. Errors are ranges from 2-3 measurements (Hung et al. 1994)

Tm values for simple sequences (e.g. d(AA):r(UU) with one type of base pair repeated for at least 24 base pairs) can be estimated from the Tm values for more complex sequences, if one assumes that the Tm values are nearest-neighbor properties.

For example, the Tm for repeating d(AA):r(UU) can be derived from the Tm's for repeating d(AAG):r(CUU) (Tm of 33.4 deg C) and for repeating d(AG):r(CU) (Tm of 43.2 deg C). Since there are three types of nearest-neighbor base pairs in d(AAG):r(CUU) [namely, d(AA):r(UU), d(AG):r(CU), and d(GA):r(UC)] and two types of nearest-neighbor base pairs in d(AG):r(CU) [namely, d(AG):r(CU) and d(GA):r(UC)], the following equation holds:

$$3 \times 33.4 \text{ deg C.} - 2 \times 43.2 \text{ deg C.} = 13.8 \text{ deg C.}$$

This equation estimates the Tm for a sequence having only the d(AA):r(UU) nearest-neighbor pair, since the contributions of the other types of nearest-neighbor base pairs have been subtracted. It can be recognized that sequence constraints on hybrid duplexes are the same as for single-stranded nucleic acids. The case is formally the same as published by Gray and Tinoco (1970), for single-stranded RNAs. The principle for deriving the sequence constraints are: (a) the properties of nearest-neighbor base pairs dominate the properties of hybrid sequences; (b) the conformations of nearest-neighbor base pairs are identical within all hybrid sequences; and (c) end effects are small. This appears to be true for polymers. Application of these principles results in only a 4% error for the 24-nucleotide long ASOs being discussed, and a proportionately lesser or greater error for sequences that are longer or shorter.

There are three equations that constrain all hybrid duplex sequences. The equations state that the number of times a given base pair precedes another base pair must equal the number of times that it follows another base pair. (N(x) is the number of the nearest-neighbors of type x, where x is the numerical label of the nearest-neighbor base pair in Table 2.)

$$N(1)+N(2)+N(3)+N(4)=N(2)+N(6)+N(10)+N(14) \quad 1.$$

[i.e. number of times U:A appears first in a nearest-neighbor equals the number of time U:A appears second]. [Note: N(2) appears on both sides of the equation, and cancels, but is included to help clarify the nature of the constraint. Similarly, there is one number that appears on both sides of each of the other constraining equations below.]

$$N(5)+N(6)+N(7)+N(8)=N(1)+N(5)+N(9)+N(13) \quad 2.$$

[i.e. number of times A:T appears first in a nearest-neighbor equals the number of time A:T appears second]

$$N(9)+N(10)+N(11)+N(12)=N(3)+N(7)+N(11)+N(15) \quad 3.$$

[i.e. number of times C:G appears first in a nearest-neighbor equals the number of time C:G appears second].

A similar equation can be written for the G:C base pair, but that equation can be derived as the sum of the above three equations. There are 16 nearest-neighbors minus 3 constraints=13 independent hybrid sequences whose properties, once known, can be used to predict the properties of all other hybrid sequences. Many sets of independent sequence combinations can be chosen. One of the simplest sets of hybrid polymer sequences is given in Table 4.

TABLE 4

An Example Set
of 13 Independent Polymer DNA:RNA Hybrid Sequences 1. poly[r(U):d(A)]
2. poly[r(A):d(T)]
3. poly[r(G):d(C)]
4. poly[r(C):d(G)]
5. poly[r(AU):d(AT)]
6. poly[r(GU):d(AC)]
7. poly[r(CU):d(AG)]
8. poly[r(GA):d(TC)]
9. poly[r(CA):d(TG)]
10. poly[r(GC):d(GC)]
11. poly[r(GAU):d(ATC)]
12. poly[r(CAU):d(ATG)]
13. poly[r(CGU):d(ACG)]

The sequences can all have phosphorothioate DNAs, or DNAs modified in any other way, as long as all occurrences of a given nearest-neighbor base pair are similarly modified. For example, data have been obtained for hybrids where the antisense DNA oligomer contains phosphorothioate linkages, i.e. S-ASOs. A complete set of 13 S-DNA:RNA hybrids was developed for use with the present invention, in which the DNA strand consists of phosphorothioate backbone linkages (S-DNA). The hybrids were formed with oligomers that were 24 nucleotides long in buffer conditions of 0.15 M potassium (phosphate), pH 7.0. Melting profiles were obtained and the melting temperatures were determined and are shown in Table 5. These data expand on the melting temperatures in Table 3, because: (a) properties for other sequences, analogous to those in Table 4 can be derived from measured nearest-neighbor properties of the sequences in Table 5; (b) the DNA strand has phosphorothioate linkages that render DNA oligomers more resistant to endogenous cellular nucleases; and (c) the buffer also includes a physiological cation concentration of 0.15 M $K^+$. The melting temperature data in Table 3 were obtained for oligomer hybrids containing normal phosphodiester linkages and were in 0.05 M sodium phosphate, pH 7.0. The new Tm data were obtained for an entire set of 13 independent hybrid sequences with S-DNA. These new data expand on the data presented hereinabove, and permit the use of the method and apparatus of the present invention for calculating the relative stabilities of hybrids formed with S-DNA antisense oligomers (S-ASOs).

The 13 hybrid sequences that have been studied and their melting temperatures are shown in Table 5. Note that the melting temperatures range from 44.1 to 66.6° C. and are significantly dependent on the sequence, for sequences having the same A+T or G+C composition. Thus, there is at least a nearest-neighbor dependence of the melting temperature.

TABLE 5

S-DNA:RNA Hybrids and Their Tm Values

| 13 Independent Sequences | Measured Tm (° C.) |
|---|---|
| 67% A + T | |
| 1 r(AGU)$_8$:S-d(ACT)$_8$ | 44.1 ± 0.2 |
| 2 r(GAU)$_8$:S-d(ATC)$_8$ | 46.9 ± 0.1 |
| 3 r(AAG)$_8$:S-d(CTT)$_8$ | 48.7 ± 1.4 |

TABLE 5-continued

S-DNA:RNA Hybrids and Their Tm Values

| 13 Independent Sequences | Measured Tm (° C.) |
|---|---|
| 50% A + T | |
| 4 r(CCUU)$_6$:S-d(AAGG)$_6$ | 44.2 ± 1.1 |
| 5 r(CU)$_{12}$:S-d(AG)$_{12}$ | 46.4 ± 0.6 |
| 6 r(CGUU)$_6$:S-d(AACG)$_6$ | 46.5 ± 0.4 |
| 7 r(GGUU)$_6$:S-d(AACC)$_6$ | 52.2 ± 1.1 |
| 8 r(GU)$_{12}$:S-d(AC)$_{12}$ | 54.4 ± 0.3 |
| 9 r(AG)$_{12}$:S-d(CT)$_{12}$ | 57.4 ± 1.5 |
| 10 r(AC)$_{12}$:S-d(GT)$_{12}$ | 57.6 ± 0.4 |
| 67% G + C | |
| 11 r(GCU)$_8$:S-d(AGC)$_8$ | 63.0 ± 0.7 |
| 12 r(AGC)$_8$:S-d(GCT)$_8$ | 64.9 ± 0.7 |
| 13 r(AGG)$_8$:S-d(CCT)$_8$ | 66.6 ± 0.5 |

Sequences were 24 base pairs long. The buffer was 0.15M potassium (phosphate), pH 7. Errors are standard deviations from 6-8 measurements (Hasham et al., 1998).

From the data of Table 5, the melting temperatures of any other independent hybrid polymer set, such as was selected for Table 4, can be derived using the nearest-neighbor formalism and the principles that end effects can be neglected. It is assumed that differences in the entropy contributions for forming the different nearest-neighbor base pairs are small compared with the magnitude of the entropy ($\Delta S°$) for a given sequence, so that melting temperatures can be treated as nearest-neighbor properties. (That is, Tm=$\Delta H°$/$\Delta S°$=constant x $\Delta H°$, where $\Delta H°$ is an accepted nearest-neighbor property.) This latter assumption is expedient for the present practical application.

The justification for these assumptions is shown in Table 6. The melting temperatures for three dependent sequences have been determined. Tm values of these sequences are compared with those calculated from the Tm values of the independent sequences in Table 5. The equations used to determine the values are shown as footnotes to Table 6. The average agreement between measured and calculated values is 1.7° C. This difference is only slightly larger than the errors involved in such Tm measurements (see Table 5) and is small compared with the total variation in Tm values of 22.5° C. for the independent sequences.

TABLE 6

Dependent
S-DNA.RNA Hybrid Sequences and a Test of the
Nearest-Neighbor Calculation of Their Tm Values

| Three Dependent Sequences | Measured Tm(° C.) | Calculated Tm(° C.) |
|---|---|---|
| 1 r(ACU)$_8$:S-d(AGT)$_8$ | 45.9 ± 0.1 | 44.3* |
| 2 r(GCUU)$_6$:S-d(AAGC)$_6$ | 54.2 ± 0.4 | 51.0** |

TABLE 6-continued

Dependent
S-DNA.RNA Hybrid Sequences and a Test of the
Nearest-Neighbor Calculation of Their Tm Values

| Three Dependent Sequences | Measured Tm(° C.) | Calculated Tm(° C.) |
|---|---|---|
| 3 r(CGU)$_8$:S-d(ACG)$_8$ | 56.7 ± 0.5 | 57.0*** |

In the calculations below, the numbers in ( ) indicate the number of the sequence in Table 5.
*Tm(r(ACU):S-d(AGT)$_8$) = [3 × Tm(1) + 3 × Tm(11) + 2 × Tm(10) − 2 × Tm(8) − 3 × Tm (12)]/3 Tm(r(ACU)$_8$:S-d(AGT)$_8$) = [3 × 44.1 + 3 × 63.0 + 2 × 57.6 − 2 × 54.4 − 3 × 64.9]/3 = 44.3
**Tm(r(GCUU)$_6$:S-d(AAGC)$_6$) = [4 × Tm(7) + 3 × Tm(11) + 2 × Tm(9) − 3 × Tm(13) − 2 × Tm(8)]/4 Tm(r(GCUU)$_6$:S-d(AAGC)$_6$) = [4 × 52.4 + 3 × 63.0 + 2 × 57.4 − 3 × 66.6 − 2 × 54.4]/4 = 51.0
***Tm(r(CGU)$_6$:S-d(ACG)$_6$) = [4 × Tm(6) + 3 × Tm(13) + 2 × Tm(8) − 4 × Tm(7) − 2 × Tm(9)]/3 Tm(r(CGU)$_6$:S-d(ACG)$_6$) = [4 × 46.5 + 3 × 66.6 + 2 × 54.4 − 4 × 52.2 − 2 × 57.4]/3 = 57.0

Thus, the nearest-neighbor calculations can be used to obtain the Tm values for other dependent hybrid sequences. That is, the Tm values of the hybrid sequences in Table 5 can be combined to give the Tm values of any nearest-neighbor combinations in other dependent oligomer hybrid sequences that are at least 24 nucleotides long (i.e., polymers). The melting temperatures derived for the hybrid polymer sequences shown below in Table 7 are for the same sequences presented in Table 4, but for which the DNAs have phosphorothioate linkages.

OPERATION

The present method of targeting the ASO (or S-ASO) sequence(s) that will form the most stable hybrid(s) is to find the one(s) that have the highest rank. The relative stabilities of the polymer sequences in Table 7 are assumed to be the same as the melting temperatures, derived as above. Other data to obtain a more accurate ranking of the 13 sequences with normal, phosphorothioate, and any other modified nucleotide linkages can also be used. For example, the free energies of hybrid formation of these, or any other independent set of polymer sequences, can be obtained to rank the polymer stabilities to be used in the procedure. Different sets of polymers with different nucleotide linkages can also be used for the particular type of nucleotide linkages in the ASOs whose stabilities are to be calculated.

The present method is composed of the steps of:

determining the fraction of each type of nearest-neighbor base pair in each target RNA:ASO-DNA hybrid sequence;

substituting the nearest-neighbor base pairs fractions into the derived formulas of Table 8 to identify the fractions of each of the 13 polymers in Table 7 that, when summed, will have the same fractions of nearest-neighbors as in the RNA:ASO hybrid;

and multiplying the fractions of the 13 polymers by the stability rank (i.e., Tm values) from Table 7 and summing the results to give the rank of a given ASO.

TABLE 7

The Set of 13 Independent Polymer S-DNA:RNA Hybrid Sequences

| | Tm(° C.) | Derivation from data in Table 5 Numbers in ( ) refer to polymers in Table 5 |
|---|---|---|
| 1. poly[r(U):S-d(A)] | 15.0 | = 4 × Tm(7) + 2 × Tm(9) − 2 × Tm(8) − 3 × Tm(13) |
| 2. poly[r(A):S-d(T)] | 31.3 | = 3 × Tm(3) − 2 × Tm(9) |
| 3. poly[r(G):S-d(C)] | 85.0 | = 3 × Tm(13) − 2 × Tm(9) |
| 4. poly[r(C):S-d(G)] | 69.0 | = 4 Tm(4) + 2 Tm(8) + 3 Tm(13) − 2 Tm(5) − 4 Tm(7) − 2 Tm(9) |
| 5. poly[r(AU):S-d(AT)] | 24.7 | = [3 × Tm(1) + 3 × Tm(2) − 2 × Tm(8) − 2 Tm(9)]/2 |
| 6. poly[r(GU):S-d(AC)] | 54.4 | = Tm(8) |
| 7. poly[r(CU):S-d(AG)] | 46.4 | = Tm(5) |
| 8. poly[r(GA):S-d(TC)] | 57.4 | = Tm(9) |
| 9. poly[r(CA):S-d(TG)] | 57.6 | = Tm(10) |
| 10. poly[r(GC):S-d(GC)] | 79.2 | = [4 × Tm(6) + 3 × Tm(11) + 3 × Tm(13) − 2 × Tm(5) − 4 × Tm(7) − 2 × Tm(9)]/2 |
| 11. poly[r(GAU):S-d(ATC)] | 46.9 | = Tm(2) |
| 12. poly[r(CAU):S-d(ATG)] | 41.5 | = [3 × Tm(2) + 2 × Tm(5) + 3 × Tm(12) − 2 × Tm(9) − 3 Tm(11)]/3 |
| 13. poly[r(CGU):S-d(ACG)] | 57.0 | = [4 × Tm(6) + 2 × Tm(8) + 3 × Tm(13) − 4 × Tm(7) − 2 × Tm(9)]/3 |

TABLE 8

Fractions of Polymers Needed to Obtain the Stability Rank of an ASO

The fractions are expressed as functions of the fractions of the nearest-neighbor base pairs that would be in the hybrid formed by the ASO. The numbering of the nearest-neighbors is as given in Table 2. Equations are analogous to those derived by Gray and Tinoco (1970) for single-stranded polymers, but herein the ASO DNA strand is considered to contain the single-strand nearest-neighbor fractions.

| Fractions of each polymer sequence | Fractions of the nearest-neighbors formed by the ASO using the 5'-3' DNA strand orientation shown in Table 2 |
|---|---|
| F(1) = F(poly[r(U):d(A)]) | = f(dAA) = f(2); see Table 2 |
| F(2) = F(poly[r(A):d(T)]) | = f(dTT) = f(5) |
| F(3) = F(poly[r(G):d(C)]) | = f(dCC) = f(16) |
| F(4) = F(poly[r(C):d(G)]) | = f(dGG) = f(11) |
| F(5) = F(poly[r(AU):d(AT)]) | = 2 × f(dTA) = 2 × f(1) |
| F(6) = F(poly[r(GU):d(AC)]) | = 2 × f(dCA) − 2 × f(Dtc) + 2 × f(dCT)<br>= 2 × f(4) − 2 × f(13) + 2 × f(8) |
| F(7) = F(poly[r(CU):d(AG)]) | = 2 × f(dAG) = 2 × f(10) |
| F(8) = F(poly[r(GA):d(TC)]) | = 2 × f(dCT) = 2 × f(8) |
| F(9) = F(poly[r(CA):d(TG)] | = 2 × f(dGT) = 2 × f(7) |
| F(10) = F(poly[r(GC):d(GC)] | = 2 × f(dGC) = 2 × f(15) |
| F(11) = F(poly[r(GAU):d(ATC)]) | = 3 × f(dTC) − 3 × f(dCT)<br>= 3 × f(13) − 3 × f(8) |
| F(12) = F(poly[r(CAU):d(ATG)]) | = 3 × f(dTG) − 3 × f(dGT)<br>= 3 × f(9) − 3 × f(7) |
| F(13) = F(poly[r(CGU):d(ACG)]) | = 3 × f(dCG) − 3 × f(dGC)<br>= 3 × f(12) − 3 × f(15) |

EXAMPLE 1

Step-by-Step Example, Comparison with Stull et al. Method.

The rank of the S-ASO sequence from the papers by Chiang et al. (1991), and Stull et al. (1992), can be used as an example of how to calculate the hybrid rank. The ranks of six 20 to 21-mers S-ASOs analyzed by Stull et al., were used to compare the present method with that of Stull et al., for determining the most stable ASOs.

Step (a): Write the DNA-ASO sequence in a 5'-to-3' orientation. The DNA is a 20-mer ASO sequence and has the following sequence (SEQ ID NO:12):

```
5' C - C - C - C - C - A - C - C - A - C - T - T - C - C - C - C - T - C - T - C 3'
   16  16  16  16  16  4   14  16  4   14  8   5   13  16  16  16  8   13  8   13 16
```

The nearest-neighbor types are labeled with the numbers as shown in Table 2. The DNA sequence would cause these nearest-neighbor base pairs to be formed when the DNA hydrogen-bonds with an RNA target. Note that the DNA sequence is 5' to 3' and that the DNA nearest-neighbors in Table 2 are on the bottom, listed 3' to 5'. Also, the ends must be closed. This is necessary to have the final numbers of nearest-neighbors be the same in the rest of the sequence as in the sum of the polymer sequences. From these labeled numbers the fraction of each type of nearest-neighbor is calculated.

| Fractions of each of the nearest-neighbors: | | |
|---|---|---|
| $f(1)$ | $= 0$ | $= f(dTA)$ |
| $f(2)$ | $= 0$ | $= f(dAA)$ |
| $f(3)$ | $= 0$ | $= f(dGA)$ |
| $f(4)$ | $= 2/20$ | $= f(dCA)$ |
| $f(5)$ | $= 1/20$ | $= f(dTT)$ |
| $f(6)$ | $= 0$ | $= f(dAT)$ |
| $f(7)$ | $= 0$ | $= f(dGT)$ |
| $f(8)$ | $= 3/20$ | $= f(dCT)$ |

| Fractions of each of the nearest-neighbors: | | |
|---|---|---|
| $f(9)$ | $= 0$ | $= f(dTG)$ |
| $f(10)$ | $= 0$ | $= f(dAG)$ |
| $f(11)$ | $= 0$ | $= f(dGG)$ |
| $f(12)$ | $= 0$ | $= f(dCG)$ |
| $f(13)$ | $= 3/20$ | $= f(dTC)$ |
| $f(14)$ | $= 2/20$ | $= f(dAC)$ |
| $f(15)$ | $= 0$ | $= f(dGC)$ |
| $f(16)$ | $= 9/20$ | $= f(dCC)$ |
| Total | $= 20/20$ | |

Step (b): Substitute the nearest-neighbor fractions in the formulas in Table 8 to obtain the fractions of each of the polymers. Note that not all of the 16 nearest-neighbor fractions need be involved in this step, because of the 3 constraints, as discussed above, that were used to derive the 13 polymer sequences used in the method herein.

| Fractions of each polymer sequence | | | |
|---|---|---|---|
| $F(1)$ | $= F(poly[r(U):d(A)])$ | $= f(2)$ | $= 0$ |
| $F(2)$ | $= F(poly[r(A):d(T)])$ | $= f(5)$ | $= 1/20$ |
| $F(3)$ | $= F(poly[r(G):d(C)])$ | $= f(16)$ | $= 9/20$ |
| $F(4)$ | $= F(poly[r(C):d(G)])$ | $= f(11)$ | $= 0$ |
| $F(5)$ | $= F(poly[r(AU):d(AT)])$ | $= 2 \times f(1)$ | $= 0$ |
| $F(6)$ | $= F(poly[r(GU):d(AC)])$ | $= 2 \times f(4) - 2 \times f(13) + 2 \times f(8)$ | $= 4/20$ |
| $F(7)$ | $= F(poly[r(CU):d(AG)])$ | $= 2 \times f(10)$ | $= 0$ |
| $F(8)$ | $= F(poly[r(GA):d(TC)])$ | $= 2 \times f(8)$ | $= 6/20$ |
| $F(9)$ | $= F(poly[r(CA):d(TG)])$ | $= 2 \times f(7)$ | $= 0$ |
| $F(10)$ | $= F(poly[r(GC):d(GC)])$ | $= 2 \times f(15)$ | $= 0$ |
| $F(11)$ | $= F(poly[r(GAU):d(ATC)])$ | $= 3 \times f(13) - 3 \times f(8)$ | $= 0$ |
| $F(12)$ | $= F(poly[r(CAU):d(ATG)])$ | $= 3 \times f(9) - 3 \times f(7)$ | $= 0$ |
| $F(13)$ | $= F(poly[r(CGU):d(ACG)])$ | $= 3 \times f(12) - 3 \times f(15)$ | $= 0$ |
| | | | Total $= 20/20$ |

Step (c): Multiply the fractions obtained in step (b) by the polymer rankings (or melting temperatures) in Table 7, and take the sum. This gives the "hybrid duplex stability rank" (or Tm) for the DNA:RNA hybrid formed with this ASO.

| Hybrid duplex stability rank | | | |
|---|---|---|---|
| 1. (poly[r(U):d(A)]) | = F(1) * 15.0 | = 0 * 15.0 | = 0 |
| 2. (poly[r(A):d(T)]) | = F(2) * 31.3 | = (1/20) * 31.3 | = 1.56 |
| 3. (poly[r(G):d(C)]) | = F(3) * 85.0 | = (9/20) * 85.0 | = 38.25 |
| 4. (poly[r(C):d(G)]) | = F(4) * 69.0 | = 0 * 69.0 | = 0 |
| 5. (poly[r(AU):d(AT)]) | = F(5) * 24.7 | = 0 * 24.7 | = 0 |
| 6. (poly[r(GU):d(AC)]) | = F(6) * 54.4 | = (4/20) * 54.4 | = 10.88 |
| 7. (poly[r(CU):d(AG)]) | = F(7) * 46.4 | = 0 * 46.4 | = 0 |
| 8. (poly[r(GA):d(TC)]) | = F(8) * 57.4 | = (6/20) * 57.4 | = 17.22 |
| 9. (poly[r(CA):d(TG)]) | = F(9) * 57.6 | = 0 * 57.6 | = 0 |
| 10. (poly[r(GC):d(GC)]) | = F(10) * 79.2 | = 0 * 79.2 | = 0 |
| 11. (poly[r(GAU):d(ATC)]) | = F(11) * 46.9 | = 0 * 46.9 | = 0 |
| 12. (poly[r(CAU):d(ATG)]) | = F(12) * 41.5 | = 0 * 41.5 | = 0 |
| 13. (poly[r(CGU):d(ACG)]) | = F(13) * 57.0 | = 0 * 57.0 | = 0 |
| Total (hybrid duplex stability rank) | | | = 67.91 |

The calculated stability rank of the sequence is 67.91 on a scale dictated by the polymer melting temperatures in Table 7. This sequence forms a relatively stable DNA:RNA hybrid.

The advantage of the method of the present invention is that it discriminates between nearest-neighbor base pairs in nucleic acid polymers such as 7 and 8 in Tables 4 and 7. Other methods used for estimating hybrid stabilities have relied on data from either DNA:DNA or RNA:RNA duplexes Chiang et al. (1991); and Stull et al. (1992). In the cases of such duplexes where both strands have the same type of backbone, there are only 8 independent sequences in the nearest-neighbor approximation (Gray and Tinoco, 1970). Any method that relies on data obtained from DNA:DNA or RNA:RNA duplexes, where both strands are the same, essentially consider polymers such as 7 and 8 in Tables 4 and 7 to have identical stabilities since they are chemically identical when both strands are identical. Such methods will be valuable for predicting the stability of hybrids only if the hybrids under study do not have a significant difference in the numbers of the nearest-neighbors that are contained in such polymers.

Comparison with Stull et al.'s Dscore

One published report by Stull et al. (1992) used a "Dscore", based on published thermodynamic stabilities of RNA:RNA duplex nearest-neighbors, to predict the inhibitory effects of S-ASOs in various experimental systems. Results, as they showed, should be in comparisons of S-ASOs of equal lengths. The most significant predictive indices were for a set of six 20 to 21-mer S-ASOs targeted against human "intracellular adhesion molecule-1" (ICAM-1) produced upon cytokine-induced expression in two cultured human cell lines (HUVEC—human umbilical vein endothelial cells, and A549—human lung carcinoma cells). Table 9 gives the six S-ASO sequences, the hybrid duplex stability scores of the present invention, Stull's Dscore, and the experimental inhibition in the two types of cells.

TABLE 9

(SEQ ID NOS 13–18, respectively)
Hybrid Rank by Tm and Dscore

| S-ASO sequence given 5' to 3' | Hybrid Rank | Stull's Dscore | % Inhibition HUVEC | A549 |
|---|---|---|---|---|
| T-G-C-C-C-A-T-C-A-G-G-G-C-A-G-T-T-T-G-A | 56.45 | −18.4 | 10 | 30 |
| C-C-T-G-T-C-C-G-G-G-A-T-A-G-G-T-T-C-A | 58.39 | −18.5 | 45 | 50 |
| C-C-C-C-C-A-C-C-A-C-T-T-C-C-C-C-T-C-T-C | 67.91 | −20.3 | 75 | 70 |
| G-C-C-C-A-A-G-C-T-G-G-C-A-T-C-C-G-T-C-A | 61.30 | −19.8 | 75 | 70 |

TABLE 9-continued (SEQ ID NOS 13—18, respectively)
Hybrid Rank by Tm and Dscore

| S-ASO sequence given 5' to 3' | Hybrid Rank | Stull's Dscore | % Inhibition HUVEC | A549 |
|---|---|---|---|---|
| G-A-C-A-C-T-C-A-A-T-A-A-A-T-A-G-C-T-G-G-T | 45.14 | −14.4 | 5 | 30 |
| T-T-G-A-G-A-A-A-G-C-T-T-T-A-T-T-A-A-C-T | 37.18 | −12.4 | 0 | 0 |

Table 10 provides the coefficients of correlation (r) for the revised stability ranks of the S-ASO sequences with the percent inhibition of the production of ICAM-1 in each type of cell culture as reported by Stull et al. (1992). Similarly, the (r) value is given for the absolute value of Stull's Dscore and compared with the percentage of inhibition. Correlation r values range from +1 for perfect correlation to −1 for negative correlation. P is the significance of the correlation coefficient using the t-test. The smaller the value of P, the more significant the correlation. That is, the null hypothesis that there is no correlation, can be rejected.

TABLE 10

Correlation Values, r, and Test of Significance

| Correlation of hybrid duplex stability rank with % inhibition | | Correlation of Dscore with % inhibition | |
|---|---|---|---|
| HUVEC Cells | A549 Cells | HUVEC Cells | A549 Cells |
| r = 0.878 | r = 0.931 | r = 0.839 | r = 0.908 |
| P < 0.02 | P < 0.01 | P < 0.05 | P < 0.02 |

As described above, and as presented in Table 10, the method of the present invention allows one to obtain a hybrid stability rank which is a better indicator than is the Dscore, for predicting the effectiveness of S-ASO sequences for inhibition of ICAM-1 expression within cells according to this limited set of data.

EXAMPLE 2

Analysis of Data in U.S. Pat. No. 5,166,195

U.S. Pat. No. 5,166,195 presents data relating to the use of oligomers to bind to the mRNA of the HIV tat protein, which trans-activates the transcription of a gene containing the "TAR" RNA element. The placental alkaline phosphatase gene (PAP) was used as a reporter gene, in a construct containing the TAR element, to assay the effectiveness of the oligomers to inhibit the production of the tat protein, and hence to inhibit the production of PAP (by preventing its trans-activation).

Six S-ASO sequences were used to inhibit PAP production, but there was no selection of which sequences should be the most effective. The method of the present invention provides such a selection and shows how the inhibition can be correlated with the sequence. Table 11 shows the sequences, the hybrid stability rank for each sequence, and the percent inhibition (average inhibition from data in FIG. 2 of the Ecker patent at 5–10 micromolar).

TABLE 11

(SEQ ID NOS 19—25, respectively)

| S-ASO sequence in Pat No. 5,166,195 | Hybrid Stability Rank | % Inhibition of PAP |
|---|---|---|
| #461 5'G-G-C-T-C-C-A-T-T-T-C-T-T-G-C-T-C-T-C-C 3' | 58.56 | 82 |
| #462 5'C-A-T-T-T-C-T-T-G-C-T-C-T-C-C-T-C-T-G-T 3' | 54.44 | 28 |
| #463 5'G-C-T-A-T-G-T-C-G-A-C-A-C-C-A-A-T-T-C 3' | 53.73 | 42 |
| #464 5'C-C-G-C-C-C-C-T-C-G-C-C-T-C-T-T-G-C-C-G 3' | 53.73 | 42 |
| #464 5'C-G-G-G-T-C-C-C-C-T-C-G-G-G-A-T-T-G-G-G 3' | 72.04 | 77 |
| #465 5'C-G-G-G-T-C-C-C-C-T-C-G-G-G-A-T-T-G-G-G 3' | 64.38 | 74 |
| #466 5'C-A-C-C-T-T-C-T-T-C-T-T-C-T-A-T-T-C-C-T 3' | 51.37 | 2 |

The stability rank has a correlation coefficient=r 0.776 (P=0.07) with the percent inhibition values. By their stability ranks, sequences #461, 464 and 465 would be predicted to be the most inhibitory. Indeed, experimental data confirm this prediction.

EXAMPLE 3

Correlation of Hybrid Stability Rank with Data for S-ASOs Against E-Selection Lesnik and Freier (1995) have published thermodynamic data on 28 oligonucleotide duplex DNA:RNA hybrids ranging from 8–21 base pairs in length having a DNA component which was not phosphorothioated. Their data were acquired in a buffer of 100 mM $Na^+$, 10 mM phosphate, 0.1 mM EDTA, and a pH of 7.1. The data indicated that under otherwise equal conditions, antisense oligonucleotides with 70–80% deoxypyrimidine content and moderate A:T/U content will be most effective at targeting structured mRNA. However, when testing this hypothesis against the biological activity for 33 antisense oligonucleotides, with phosphorothioated backbones, targeted to different regions of human E-selectin and VCAM-1 mRNAs, these authors reported that no simple correlation between antisense activity and hybridization properties of DNA oligonucleotides to single-stranded RNA targets in solution existed because many other factors affect activity of antisense oligonucleotides. It should be noted that the genes encoding E-selectin and vascular cell adhesion molecule-1, or VCAM-1, are two of a group of genes that encode proteins that are induced on the luminal surface of vascular endothelium in response to inflammatory stimuli. Data were taken from Bennett et al., 1994.

However, as discovered by the present inventors, the data presented by Bennett et al. (1994) for the inhibition by the nine antisense oligonucleotides directed to the 5'-untranslated region, AUG start codon, and coding regions of the E-selectin gene do show a significant correlation to hybrid stability using the present method of ranking hybrid stabilities. These S-ASOs are listed in Table 12 below along with the calculation of the relative hybrid stabilities and the % inhibition of E-selectin.

The correlation coefficients between the inhibition values and the calculated hybrid duplex stability ranks is given in Table 13. Also shown are the correlation coefficients between the % inhibition values and % deoxypyrimidine, and between the inhibition values and % G+C contents, proposed by Lesnik and Freier (1995) to be a guide for selecting effective ASOS.

TABLE 13

Correlation of % Inhibition of E-selection

| With Hybrid Duplex Stability Rank | With % Deoxypyrimidine | With % G + C |
|---|---|---|
| 0.851 | 0.615 | 0.766 |
| P = 0.004 | P = 0.08 | P = 0.02 |

The correlation of % inhibition of E-selection with the hybrid duplex stability rank is highly significant at P<0.01 and better than the correlations with the other simpler estimates of stability.

EXAMPLE 4

Prediction of Better S-ASO to Block Gag mRNA

HIV-1 retrovirus gene "Gag" encodes a glycosaminoglycan that functions as a virion core protein. The mRNA sequence is shown in Table 14 for the region surrounding the AUG start codon of Gag. Also shown in Table 14 is a 25-mer S-ASO that has been shown to inhibit HIV-1 replication (Lisziewicz et al., 1994). It is designated "GEM91", for Gene Expression Modulator 91. Using the methodology of the present invention, it has a hybrid stability rank of 59.9. A shift of just four nucleotides would give an S-ASO with a stability rank of 62.6 which is referred to as "GEM91-Optimal." From the correlations presented above for the predictive ability of the hybrid stability rank in three other systems, there could be an increase of 2.9% inhibition/unit increase in hybrid stability rank. That is, GEM91-Optimal could show (62.2−59.9)×2.9=6.67% increase in inhibition of antiviral replication. The method of the present invention therefore reveals the possibility of such inhibition enhancement during the design of S-ASO sequences.

TABLE 12

(SEQ ID NOS 26–34, respectively)

| S-ASO sequence in Bennet et al. (994) | Hybrid Stability Rank | % Inhibition of E-Selectin |
|---|---|---|
| #4764 (Target: 5'-untranslated region) 5'G-A-A-G-T-C-A-G-C-C-A-A-G-A-A-C-A-G-C-T 3' | 51.62 | 49.8 |
| #2687 (Target: 5'-untranslated region) 5'T-A-T-A-G-G-A-G-T-T-T-T-G-A-T-G-T-G-A-A 3' | 40.86 | 26.2 |
| #2679 (Target: 5'-untranslated region) 5'C-T-G-C-T-G-C-C-T-C-T-G-T-C-T-C-A-G-G-T 3' | 61.37 | 93.4 |
| #4759 (Target: 5'-untranslated region) 5'A-C-A-G-G-A-T-C-T-C-T-C-A-G-G-T-G-G-G-T 3' | 54.80 | 79.8 |
| #2683 (Target: AUG codon) 5'A-A-T-C-A-T-G-A-C-T-T-C-A-A-G-A-G-T-T-C-T 3' | 43.90 | 46.6 |
| #2686 (Target: AuG codon) 5'T-G-A-A-G-C-A-A-T-C-A-T-G-A-C-T-T-C-A-A-G 3' | 45.81 | 48.6 |
| #4756 (Target: splice junction; coding region) 5'C-C-A-A-A-G-T-G-A-A-G-A-G-C-T-G-A-G-A-G-A 3' | 49.89 | 64.3 |
| #4732 (Target: coding region) 5'C-T-G-A-T-T-C-A-A-A-G-G-C-T-T-T-G-G-G-C-A-G 3' | 52.95 | 44.7 |
| #4730 (Target: splice junction; 3' region) 5'T-T-C-C-C-C-A-G-G-A-T-G-C-A-C-C-T-G-T-T-T 3' | 55.87 | 97.7 |

TABLE 14

(SEQ ID NOS 35—37, respectively)

mRNA: GACUAGCGGAGGCUAGAAGGAGAGAGAUGGGUGCGAGAGCGUCAGUAUUAAGCGGGGG
S-ASO "GEM91":       TCTTCCTCTCTCTACCCACGCTCTC
S-ASO "GEM91-Optimal":   CCTCTCTCTACCCACGCTCTCGCAG

EXAMPLE 5

Extension of the Method to the Analysis of Triplex-Forming Sequences and Antigene Oligomers The present invention can be readily extended to predict the most stable triplex-forming sequences, or antigene oligomers (AGOs). It is known that certain duplex DNA genome sequences can be attached by a third oligonucleotide strand to form a triplex sequence. The most common types of triplex sequences are illustrated in Table 15. The third strand of Triplex A is paired by Hoogsteen pairing to the purine strand of the usual Watson-Crick pair. The third strand of Triplex B is probably paired by reverse-Hoogsteen pairing to the purine strand of the Watson-Crick pair to form base triples (Pilch et al., 1991; Laughton and Neidle, 1992). The illustrations are for DNA and well-known types of triplets, but the concepts can be readily extended to other triplexes with different base-pairing and to triplets having one or more non-DNA strands, or strands modified with different nucleotide linkages.

It is recognized that the same theory of Gray and Tinoco (1970) can be used with the apparatus and method of the present invention to calculate the number of independent third strand sequences in such cases. The number of independent third strand sequences is restricted in exactly the same way as are single-strand sequences, because there is no symmetry in the overall triplex structure. For two types of triplets (Triplex A in Table 15), there are 3 independent triplex sequences, and for three types of triplets (Triplex B in Table 15), there are 7 independent sequences. Examples of sets of independent sequences are listed in Table 16 for these two types of triplexes.

TABLE 16

Example sets of independent triplex DNA:DNA:DNA
Example sets of independent triplex DNA:DNA:DNA
sequences for the two types of triplexes
illustrated in Table 15. The sequence in the
third strand is given first for each triplex
polymer sequence. Sequences are given for all
three strands in the 5'-to-3' direction.

Tentative stability rank (Triplex A) Two type of base triples. Three (3) independent sequences are required.

1. poly[d(T):d(A):d(T)]      3 (highest)

TABLE 15

Illustration of Two Types of DNA Triplexes

Triplex A.
Third strand parallel to Watson-Crick purine strand. The base triplets
are C:G:C and T:A:T. (The non-Watson-Crick third strand nucleotide is
given first.) (11 + 11 indicates that the
cytosines in a third strand are protonated.)

Third strand (Pyrimidines C and T): 3' -------
C+T --------- 5'
Watson-Crick Purine strand (G and A): 3' -------
GA ---------- 5'
Watson-Crick Pyrimidine strand (C and T): 5'
------- CT ---------- 3'
                    Triplex B.
    Third strand anti-parallel to Watson-Crick purine strand. Common
             base triplets are G:G:C:, A:A:T, and T:A:T.

Third strand (purines G,A, and pyrimidine T):
5'----- AGT ------- 3'
Watson:Crick Purine strand (G and A): 3'-----
AGA ------- 5'
Watson:Crick Pyrimidine strand C and T): 5'-----
TCT ------- 3'

TABLE 16-continued

Example sets of independent triplex DNA:DNA:DNA
Example sets of independent triplex DNA:DNA:DNA
sequences for the two types of triplexes
illustrated in Table 15. The sequence in the
third strand is given first for each triplex
polymer sequence. Sequences are given for all
three strands in the 5'-to-3' direction.

|  | Tentative stability rank |
|---|---|
| 2. poly[d(C+):d(G):d(C)] | 1 (lowest) |
| 3. poly[d(TC+):d(AG):d(CT)] | 2 |

(Triplex B) Three types of base triples. Seven (7) independent sequences are required.

1. poly[d(A):d(A):d(T)]
2. poly[d(T):d(A):d(T)]
3. poly[d(G):d(G):d(C)]
4. poly[d(AT):d(AA):d(TT)]
5. poly[d(AG):d(GA):d(TC)]
6. poly[d(GT):d(AG):d(CT)]
7. poly[d(ATG):d(GAA):d(TTC)]

The stabilities of the three independent sequences of Table 16A are tentatively ranked on the basis of data at pH 7.4 by Kiessling et al., 1992. The method of analysis provides direction to obtaining the type of information that is both sufficient and necessary for determining the most stable triplex sequences. (Kiessling et al. (1992) determined the relative stabilities of the eight possible combinations of three successive base triples in the motif of Table 16A. They did not recognize that the sequences were interrelated and that their eight measured values were also interrelated.) The analysis can be expanded to include other types of base pair mismatches at each position (i.e. third strand bases that do not form the base triples listed above).

The method used for ranking the independent hybrid is with the assumption that the end effects are relatively small. That is, melting temperatures, or thermodynamic properties, should be obtained for sequences that are approximately 20 base pairs (or base triplets) long, so that the ends are 5% of the total sequence. Below, it is shown how to expand the method in general to short sequences.

EXAMPLE 6

Analyzing Short Hybrid Sequences with End Effects

The expanded theory as shown below, demonstrates that if end effects must be taken into account, the stabilities of DNA:RNA hybrids (of varying length and with the four normal base pairs) must be obtained for 20 independent sequences. Therefore, the method described above in detail is based upon 13 polymer sequences (or long sequences) and is currently the most practical method for obtaining stabilities of hybrid sequences. But the method can be applied to a larger data set using shorter sequences should such data become available.

Some elements of a procedure for determining the number of independent sequences of short duplex sequences, with end effects, has been described by Goldstein and Benight (1992). However, they did not apply the procedure to single-stranded sequences, and their procedure did not specify how to include sequences of varying versus fixed length.

The end (E) is treated like any other base (or base pair) There will be 5×5=25 different nearest-neighbors whose properties one would like to obtain. Ends do not appear next to each other, which adds an additional constraint, but otherwise the constraint equations (the number of times one base comes before another must equal the number of times it comes after another base) are analogous to those for single-strands containing only the four usual bases.

TABLE 17

Equations

1. N(EE) = 0 (a special equation for the ends)
2. N(AA) + N(AT) + N(AG) + N(AC) + N(AE) = N(AA) + N(TA) + N(GA) + N(CA) + N(EA)
3. N(TA) + N(TT) + N(TG) + N(TC) + N(TE) = N(AT) + N(TT) + N(GT) + N(CT) + N(ET)
4. N(GA) + N(GT) + N(GG) + N(GC) +N(GE) = N(AG) + N(TG) + N(GG) + N(CG) + N(EG)
5. N(CA) + N(CT) + N(CG) + N(CC) + N(CE) = N(AC) + N(TC) + N(GC) + N(CC) + N(EC)
6. N(AE) + N(TE) + N(GE) + N(CE) = N(EA) + N(ET) + N(EG) + N(EC)

Since equations 2+3+4+5=6, there are only 5 linearly independent equations. Therefore, the number of independent sequences of DNA:RNA hybrids that can vary in length is 25−5=20. As in the case of polymers of infinite length, it is not possible to determine the properties of all 25 individual nearest-neighbors (including the ends), but using the present invention one can obtain the properties of 20 independent sequence combinations from which the property of any other dependent sequence, of any length, can be obtained (Gray, 1997a).

EXAMPLE 7

Example of Application of the Present Method to Obtain Thermodynamic Parameters.

The following illustrates one application of the method of the present invention wherein thermodynamic values for 20 combinations of nearest-neighbor base pairs of DNA:RNA hybrid sequences with ends were determined and compared to recently published thermodynamic measurements of oligomers (Sugimoto et al., 1995). The data reported by Sugimoto are for nucleic acids having normal phosphodiester bonds, and for oligomers in 1 M NaCl (which is non-physiological). However, these considerations do not impact the analysis and principles described in this example.

Sugimoto et al. (1995) measured the thermodynamic values for 64 different DNA:RNA hybrid sequences, and performed a least-squares fit of these values to 16 hybrid base pair nearest-neighbors (Table 2, hereinabove) plus one initiation parameter. Tabulated values from their Table 3 are listed below, but with the nearest-neighbors rearranged to be in the same order as in the present application.

TABLE 18

| Nearest-Neighbor Sequence* | ΔH° (kcal/mol) | ΔS° (cal/(mol °K.)) | ΔG° (37° C.) (kcal/mol) |
|---|---|---|---|
| rUA/dAT | −7.8 | −23.2 | −0.6 |
| rUU/dAA | −11.5 | −36.4 | −0.2 |
| rUC/dGA | −8.6 | −22.9 | −1.5 |
| rUG/dCA | −10.4 | −28.4 | −1.6 |
| rAA/dTT | −7.8 | −21.9 | −1.0 |
| rAU/dAT | −8.3 | −23.9 | −0.9 |
| rAC/dGT | −5.9 | −12.3 | −2.1 |
| rAG/dCT | −9.1 | −23.5 | −1.8 |
| rCA/dTG | −9.0 | −26.1 | −0.9 |
| rCU/dAG | −7.0 | −19.7 | −0.9 |
| rCC/dGG | −9.3 | −23.2 | −2.1 |
| rCG/dCG | −16.3 | −47.1 | −1.7 |
| rGA/dTC | −5.5 | −13.5 | −1.3 |
| rGU/dAC | −7.8 | −21.6 | −1.1 |
| rGC/dGC | −8.0 | −17.1 | −2.7 |
| rGG/dCC | −12.8 | −31.9 | −2.9 |
| Initiation | +1.9 | −3.9 | +3.1 |

(taken from Table 3 of Sugimoto et al. (1995)
*Sequences in both strands written 5' to 3'

It should be noted that there are 5 constraints on the 25 combinations of nearest-neighbors (the 16 nearest-neighbors listed in the above Table 2 and Table 18 plus 9 types of nearest-neighbor ends represented as base pairs next to ends: rUE/dEA, rAE/dET, rCE/dEG, rGE/dEC, rEU/dEA, rEA/dTE, rEC/dGE, rEG/dCE and rEE/dEE, where the "end" base pair is E/E). The five constraints are described in Table 17 above and its discussion. Thus, there are 20 (25−5=20) combinations of nearest-neighbor properties that can really be derived from measurements on oligomer sequences. Sugimoto et al. (1995) make the usual assumption of combining the properties of all possible types of base pairs next to ends into one "initiation" parameter. Although they assign values to the 17 resulting parameters (16 nearest-neighbors plus one initiation parameter), these values do not represent a unique or optimal solution to the problem of obtaining a list of thermodynamic values that can then be used to predict thermodynamic values for other sequences, since there are 20 parameters needed to define all possible sequences.

Table 19 shows the independent oligomer sequence combinations whose thermodynamic values can be assigned from the data published by Sugimoto et al. (1995) for 64 oligomer sequences. Values are assigned only to combinations of nearest-neighbors but not to individual nearest-neighbors. The values were derived using a singular value decomposition program (Press et al., 1992) to do the least squares fit and are described in Gray (1997b).

TABLE 19

Thermodynamic Values of 20 Nearest-Neighbor Combinations

| Independent Oligomer Nearest-Neighbor Combination* | ΔH° (kcal/mol) | ΔS° (cal/(mol °K.)) | ΔG° (37° C.) (kcal/mol) |
|---|---|---|---|
| rEUAE/dETAE | −12.9 | −48.4 | 2.1 |
| rEUUE/dEAAE | −8.3 | −34.5 | 2.4 |
| rEUCE/dEGAE | −12.7 | −45.8 | 1.5 |
| rEUGE/dECAE | −11.5 | −42.0 | 1.5 |
| rEAAE/dETTE | −11.7 | −44.7 | 2.1 |
| rEAUE/dEATE | −11.9 | −45.5 | 2.2 |
| rEACE/dEGTE | −14.2 | −49.9 | 1.3 |
| rEAGE/dECTE | −13.1 | −47.1 | 1.5 |

TABLE 19-continued

Thermodynamic Values of 20 Nearest-Neighbor Combinations

| Independent Oligomer Nearest-Neighbor Combination* | ΔH° (kcal/mol) | ΔS° (cal/(mol °K.)) | ΔG° (37° C.) (kcal/mol) |
|---|---|---|---|
| rECAE/dETGE | −13.0 | −47.6 | 1.8 |
| rECUE/dEAGE | −8.2 | −32.4 | 1.8 |
| rECCE/dEGGE | −12.8 | −44.3 | 1.0 |
| rECGE/dECGE | −17.8 | −61.1 | 1.2 |
| rEGAE/dETCE | −14.8 | −51.7 | 1.3 |
| rEGUE/dEACE | −13.7 | −49.3 | 1.6 |
| rEGCE/dEGCE | −17.0 | −56.2 | 0.5 |
| rEGGE/dECCE | −16.5 | −54.6 | 0.5 |
| rEUE/dEAE | −3.0 | −18.3 | 2.7 |
| rEAE/dETE | −5.2 | −26.7 | 3.1 |
| rECE/dEGE | −6.9 | −31.9 | 3.0 |
| rEGE/dECE | −6.2 | −30.1 | 3.2 |

*Sequences in both strands written 5' to 3'

The thermodynamic values for specific nearest-neighbor base pairs cannot be determined (except for the homopairs rUU/dAA, rAA/dTT, rCC/dGG, and rGG/dCC). Nevertheless, the values for the 20 combinations in Table 19 can be combined to calculate the thermodynamic parameters for any other sequence. For example, the ΔG° for the sequence r(EUGAAE)/d(ETTCA) is:

$$\Delta G°[r(EUGAAE)/d(ETTCA)] = \Delta G°[rEUGE/dECAE] + \Delta G°[rE\text{-}GAE/dETCE] + \Delta G°[rEAAE/dETTE] - \Delta G°[rEGE/dECE] - \Delta G°[rEAE/dETE] = -1.4 \text{ kcal/mol}$$

This equation is just the addition of the ΔG° values of all the nearest-neighbors in the sequence, minus those of the overlapping base pair-plus-ends for the interior base pairs, to balance the nearest-neighbors in the equation. Note that the resulting free energy is negative (i.e. favorable) for formation of this short duplex, even though the listed free energy values in Table 19 are positive.

Increased accuracy of the method of the present invention for obtaining thermodynamic parameters is described as follows. Using the values derived by Sugimoto et al. (1995) in Table 18 and the values in Table 19, the values of the 64 oligomers can be calculated and compared with the original, experimental values. Table 20 gives the standard deviations from the experimental values of those calculated from each set of derived values.

TABLE 20

Standard Deviations of Recalculated Thermodynamic Values for the Experimental Values of 64 Oligomers

| Calculation Method | ΔH° (kcal/mol) | ΔS° (cal/(mol °K)) | ΔG°(37° C.) (kcal/mol) |
|---|---|---|---|
| Sugimoto et al. | 5.8 | 19.1 | 0.45 |
| Table 19 | 4.3 | 13.5 | 0.31 |

All of the thermodynamic parameters are more accurately predicted using the methodology of the present invention. The method and apparatus of the present invention take end effects into account, and do not require the extraction of explicit values for each nearest-neighbor base pair. The 64 sequences for which thermodynamic values were calculated ranged from 5 to 12 base pairs in length, with most being 8 base pairs in length. The decrease in error of ΔG°(37° C.) of about 0.14 kcal/mol reflects a difference of at least 0.28 kcal/mol for typical antisense sequences that are 16 or more base pairs in length.

The relation of percentage hybridization effectiveness of an antisense oligomer to the ΔG° is calculated as follows.

The equilibrium constant for:

ASO+mRNA Target←—→ASO:mRNA hybrid is related to the free energy and is given by the equation:

$$Keq = [ASO:mRNA\ hybrid]/([ASO][mRNA]) = e^{-\Delta G°/RT},$$

where R is the gas constant (1.987 cal/(mol K)) and T is the absolute temperature. Taking the [ASO] concentration to be 100 nM and to be in excess over the target mRNA concentration (following the analysis of Freier et al., 1992), then $$[ASO:mRNA\ hybrid]/[mRNA] = [ASO]e^{-\Delta G°/RT} = 10^{-7}e^{-\Delta G°/RT}.$$

Thus, if one has an ASO sequence and conditions leading to a 50% hybridization at 37° C., the ΔG°=−RT ln (0.5× $10^{+7}$)=−9.5° 10 kcal/mol. A difference of +/−0.28 kcal/mol would result in hybridizations of:

$$[ASO:mRNA\ hybrid]/[mRNA] = 10^{-7}e^{+(9.5\pm 0.28)/RT} = 0.32\ to\ 0.78\ or\ 32\%\ to\ 78\%.$$

This example shows that, due to the exponential relation between the equilibrium constant and ΔG°, the application of the method of the present invention described herein is useful in calculating thermodynamic values for hybrid formation, leading to an improvement in the percentage of hybridization predicted by 18 to 28 percent (i.e. 50% versus 32 or 78%).

EXAMPLE 8

Nearest-Neighbor Thermal Stability Apparatus and Method

The Nearest-Neighbor Thermal Stability Analysis apparatus and method (NNTSA v0.9) of the present invention processes data for use in calculating thermal melting temperatures for phosphorothioate DNA:RNA hybrids. The program relies on melting temperature data or ΔG° data for hybrids of phosphorothioate DNA 24-mers (24 nucleotides long) mixed with complementary RNAs of the same length in a 0.15 M potassium buffer at physiologic pH (pH 7). Tm data predicted for other length hybrid duplexes are roughly estimated based on extrapolation of studies using 12-mers and 24-mers. The NNTSA program can be stored on distribution disk which can contain 12 files:

(1) Setup.ex_(Part of installation program)
(2) Setup.1st (Part of installation program)
(3) NNTSA9.ex_(Compressed main program)
(4) DATA.in_(Compressed program data file)
(5) TEST.se_(Compressed sample input file)
(6) VBRUN300.dl_(Compressed program library)
(7) CMDIALOG.vb_(Compressed program library)
(8) GRID.vb_(Compressed program library)
(9) SETUP.ex_(Installation program)
(10) SETUPKIT.dl_(Compressed installation library)
(11) COMMDLG.dl_(Compressed program library)
(12) VER.dl_(Compressed installation library)

After installation of the NNTSA program from the above-described distribution disks, a target computer will contain the following files:

(1) NNTSA9.exe (Working program)
(2) DATA.ini (Program data file)
(3) TEST.seq (Sample program input file)
(4) VBRUN300.dll (Program library, in windows system folder)
(5) CMDIALOG.vbx (Program library, in windows system folder)
(6) GRID.vbx (Program library, in windows system folder)
(7) COMMDLG.dll (Program library, in windows system folder)

System Requirements:

A 386 or higher processor (486 or higher recommended) based PC running Microsoft Windows 3.1 or later may be used having 4 MB of RAM and 2 MB free hard disk space. A math co-processor is not required. A 486DX2-66 can process a sequence of 2500 bases in about 2 minutes. It should be noted that any type of electronic processor can be used in combination with a compatible program capable of operating according to the invention. Examples of storage media that can be used with the present invention include, but are not limited to: magnetic tape, optical disk, compact disk, hard disk, floppy disk, ferroelectric memory, optical storage, electrically eraseable programmable read only memory (EEPROM), flash memory, read only memory (ROM), static random access memory (SRAM), dynamic random access memory (DRAM), ferromagnetic memory, charge coupled devices, smart cards, and like storage media.

STEPWISE PROCEDURE FOR OPERATING NNTSA

Program Start-Up:

The present example uses the Windows operating system as an example, but other operating systems can be used with the present invention. The NNTSA can be installed on either an internal or external disk, or memory storage medium. After installation, the program is started up either by double-clicking on the NNTSA icon or entering appropriate keyboard commands.

Upon start-up, the main NNTSA program will come up in a window. To perform an analysis enter the length of the antisense sequence to use for analysis (the default is 24 bases) in the field labeled "Oligo Length". Next, the length of the RNA sequence to be analyzed is entered. For example, this sequence can be less than the total length of the RNA, e.g., if the mRNA has 3000 bases, 100 can be entered to analyze only the first 100 bases. Any number greater than the length of the oligo and equal to or less than the total length of the RNA can be used up to 4000 bases. The user can then choose whether to use length dependent correction by selecting the appropriate button in the "Options" dialog box (this is accessed by clicking on the OPTIONS button at the bottom of the main program window). The program is now ready to read in data.

Reading or Entering Data into NNTSA:

The apparatus and method of the present invention allows the program to accept RNA sequences in text file format denoted as SEQ (the exact format of the SEQ file is noted below) or RNA sequences can be entered manually. To read a SEQ file into NNTSA and perform an analysis, the user can click on the "Read Data From File" button and following the appropriate commands, or data can be entered manually into NNTSA by clicking on the "Enter mRNA by Hand" button and entering into a dialog box the RNA sequence to be analyzed in a 5' to 3' direction. The user will enter at least the number of bases specified in the "mRNA Length" text box located in the main program window. Analysis of the hand-entered sequence then begins in the main program window.

Analyzing and Saving Results:

After the analysis of the data is complete, several aspects of the main program window will change. The user will now be presented with a scroll bar under the POSITION text box (if the number of bases in the mRNA is greater than the length of the oligo). This scroll bar can be used to move up and down the mRNA sequence and view the results of the analysis. The number in the position text box indicates the beginning position on the mRNA of an oligomer of the length specified by the user previously. The sequence of the mRNA position can be read from the SEQUENCE text box in the main program window and is written 5' to 3'. The calculated melting temperature of the hybrid can also be read from the main program window.

The results of the analysis can be saved as a text file using standard commands and conventions. This saved output can be opened by almost any graphing program which can import comma delimited text (such as DeltaGraph, Excel or SigmaPlot). The programs can be used to create a plot of the results.

EXAMPLE 9

Saving File Format Files

File Format for SEO Text Files:

To save an mRNA sequence, a file must be in the proper format so as to be read in by NNTSA. This format is simply a text file wherein the information is properly arranged. One exemplary embodiment of a SEQ file is shown below (SEQ ID NO:38):

CUGCAGAAAUAACUAGGUACUAAGCCCGUUUGU
GAAAAGUGGCCAAACCCAUAAAUUUGGCAAUUA
CAAUAAAGAAGCUAAAATUGUGGUCAAACUC
ACAAACAUUUUUAUUAUAUACAUUUUAGUA
GCUGAUGCUUAUAAAAGCAAUAUUUAAAUCGUA
AACAACAAAUAAAAUAAAAUUUAAACGAUGUGA
UUAAGAGCCAAAGGUCCUCUAGAAAAAGGUAU
UUAAGCAACGGAAUUCCUUUGUGUUAGUACUA
UUUUAACGAAUAAUAAAAUCAGGUAUAGGUA
ACUAAAAA

In this particular embodiment, the file can contain a header of any length followed by a colon (:) and then the sequence. In the present embodiment of the NNTSA program, the SEQ file will not contain any spaces, carriage returns, or end of line characters. The colon tells the program where to begin reading in sequence data. Anything before the colon is ignored in the analysis. The sequence of the mRNA can be entered by hand or copied from nucleic acid databases and pasted into a word processor text file. Many word processing programs such as Microsoft Word, Wordperfect, and the like can be used. After the data have been entered the file has to be saved with an extension of SEQ so the program (NNTSA) will recognize it in the "Read Data From File" dialog box.

Length-Dependence Correction:

As described by Cantor and Schimmel (1980), for a homologous series of sequences (e.g., $A_nU_n$: $A_nU_n$), the melting temperature increases with length. The equation describing this relationship is generally:

$$1/Tm=A+B/N,$$

where N is the chain length, and A and B are constants for a given set of experimental conditions. Tm data were acquired for $S-d(AC)_n:r(GU)_n$, where N(1)=12 and N(2)=24, and substituted into the above equation;

$$1/Tm(1)=A+B/N(1),$$

and $$1/Tm(2)=A+B/N(2).$$

This gives:

$$1/Tm(1)-B/N(1)=1/Tm(2)-B/N(2),$$

and $$B=[1/Tm(1)-/Tm(2)]/[1/N(1)-1/N(2)]=2.2\times10^{-4}/0.0417=5.28\times10^{-3}.$$

Therefore, for any other length N(3), assuming that the relationship is identical for all sequences.

$$[1/Tm(\text{Calc length N})-1/Tm(\text{Calc 24-mer})]/[1/N-1/24]=B;$$

and $$Tm(\text{Calc length N})=\{1/Tm(\text{Calc 24-mer})+[1/N-1/24]*5.28\times10^{-3}\}^{-1}.$$

---

Source Code for Nearest-Neighbor Thermal Stability Analysis

```
Sub Command1_Click ()
form4.Hide
EndSub
Sub Command1_Click ()
Form6.Hide
End Sub
Sub Command1_Click ()
On Error GoTo ErrorTrap:
    form3.Hide
form1.Label24.Visible = 1
If (Val(form1.Text20.Text) - Val(form1.Text 19.Text)) <= 0 Then
    form1.HScroll1.Max = 1
    form1.HScroll1.Visible = 0
    Else
            form1.Hscroll1Max = Val (form1.Text20.Text) -
Val(form1.Text19.Text) + 1
            form1.Hscroll1.Visible = 1
    form1.Label24.Visible = 1
    form1.Label23.Visible = 0
        form1.Refresh
            End If
datafile = "data.ini"
open datafile for Input As #1
Input #1, slope
Input #1, tm1
Input #1, tm2
Input #1, tm3
Input #1, tm4
Input #1, tm5
Input #1, tm6
Input #1, tm7
Input #1, tm8
Input #1, tm9
Input #1, tm10
Input #1, tm11
Input #1, tm12
Input #1, tm13
Close #1
tempname = "temp.in"
Open tempname For Output As #1
Print #1, " " Text1.Text
Close #1
Open tempname For Input As #1
headstart:
header = Input$(1, #1)
If header <>" " Then
Go To headstart:
End If
datastart = Seek (1)
mmalength = Val(form1.Text20.Text)
seekposition = datastart
Seek#1, seekposition
```

Source Code for Nearest-Neighbor Thermal Stability Analysis

```
Do Until seekposition>=mmalength - length + datastart + 1
i = 0
NN1 = " "
ist = " "
buffer = " "
length = Val(form1.Text19.Text)
OLIGO(q) = Input$ (length, #1)
Seek#1, seekposition
getist:
ist = Input$ (1, #1)
If ist = "a" Then
    ist = "A"
End If
If ist = "c" Then
    ist = "C"
End If
If ist = "g" Then
    ist = "G"
End If
If ist = "u" Then
    ist = "U"
End If
If ist = "t" Then
    ist = "U"
End If
If ist = "T" Then
    ist = "U"
End If
If ist "A" And ist "G" And ist "C" And ist "U" Then
    GoTo getist:
        End If
NN1 = ist
For i = 2 To length
begin:
buffer = Input$ (1, #1)
If buffer = "a" Then
    buffer = "A"
End If
If buffer = "c" Then
    buffer = "C"
End If
If buffer = "g" Then
    buffer = "G"
End If
If buffer = "u" Then
    buffer = "U"
End If
If buffer = "t" Then
    buffer = "U"
End If
If buffer = "T" Then
    buffer = "U"
End If
If ist "A" Ahd ist "G" And ist "C" And ist "U" Then
    Go To begin:
        End If
If ist = " " Then Go To begin:
If ist = Chr (13) Then Go To begin:
If ist = Chr (10) Then Go To begin:
continue:
If buffer = "A" Then
If NN1 = "A" Then
    AAarray(q) = AAarray(q) + 1
        End If
If NN1 = "C" Then
    Caarray(q) = Caarray(q) + 1
        End If
If NN1 = "G" Then
    GAarray(q) = Gaarray(q) + 1
        End If
If NN1 = "U" Then
    UAarray(q) = Uaarray(q) + 1
        End If
    NN1 = "A"
End If
If buffer = "C" Then
    Gccontent(q) = GCcontent(q) + 1
```

Source Code for Nearest-Neighbor Thermal Stability Analysis

```
    Ccontent(q) = Ccontent(q) + 1
If NN1 = "A" Then
    ACarray(q) = ACarray(q) + 1
End If
If NN1 = "C" Then
    CCarray(q) = CCarray(q) + 1
End if
If NN1 = "G" Then
    GCarray(q) = GCarray(q) + 1
End If
If NN1 = "U" Then
    UCarray(q) = UCarray(q) + 1
End If
    NN1 = "C"
End If
If buffer = "G" Then
    GCcontent(q) = GCcontent(q) + 1
    Gcontent(q) = Gcontent(q) + 1
If NN1 = "A" Then
    AGarray(q) = AGarray(q) + 1
End If
If NN1 = "C" Then
    CGarray(q) = CGarray(q) + 1
End If
If NNI = "G" Then
    GGarray(q) = GGarray(q) + 1
End If
If NN1 = "U" Then
    UGarray(q) = UGarray(q) + 1
End If
    NN1 = "G"
End If
If buffer = "U" Then
    If NN1 = "A" Then
        AUarray(q) = AUarray(q) + 1
        End If
    If NN1 = "C" Then
    CUarray(q) = Cuarray(q) + 1
    End if
    If NN1 = "G" Then
    GUarray(q) = GUarray(q) + 1
    End if
    If NN1 = "U" Then
    UUarray(q) = UUarray(q) + 1
    End if
        NN1 = "U"
End If
Next i
Rem*******last NN pair (imaginary)************
If ist = "A" Then
    If buffer = "A" Then
        AAarray(q) = AAarray(q) + 1
    End If
    If buffer = "C" Then
        CAarray(q) = CAarray(q) + 1
    End If
    If buffer = "G" Then
        GAarray(q) = GAarray(q) + 1
    End If
    If buffer = "U" Then
        UAarray(q) = UAarray(q) + 1
    End If
End If
If ist = "C" Then
    GCcontent (q) = GCcontent(q) + 1
    Ccontent(q) = Ccontent(q) + 1
    If buffer = "A" Then
        ACarray(q) = ACarray(q)) + 1
    End If
    If buffer = "C" Then
        CCarray(q) = CCarray(q) + 1
    End If
    If buffer = "G" Then
        Gcarray(q) = GCarray(q) + 1
    End If
    If buffer = "U" Then
        UCarray(q) = UCarray(q) + 1
```

Source Code for Nearest-Neighbor Thermal Stability Analysis

```
            End If
        End If
If ist = "G" Then
    GCcontent(q) = GCcontent (q) + 1
    Gcontent (q) + Gcontent(q) + 1
    If buffer = "A" Then
        AGarray (q) = AGarray(q) + 1
    End If
    If buffer = "C" Then
        CGarray(q) = CGarray + 1
    End If
    If buffer = "G" Then
        GGarray(q) = GGarray + 1
    End If
    If buffer = "U" Then
        UGarray(q) = UGarray + 1
    End If
End If
If ist = "U" Then
    If buffer = "A" Then
        AUarray(q) = AUarray(q) + 1
    End If
    If buffer = "C" Then
        CUarray(q) = Cuarray(q) + 1
    End If
    If buffer = "G" Then
        GUarray(q) = GUarray(q) + 1
    End If
    If buffer = "U" Then
        UUarray(q) = UUarray(q) + 1
    End If
form1.Text1.Text = AAarray (q)
form1.Text2.Text = ACarray (q)
form1.Text3.Text = AGarray (q)
form1.Text4.Text = AUarray (q)
form1.Text5.Text = CAarray (q)
form1.Text6.Text = CCarray (q)
form1.Text7.Text = CGarray (q)
form1.Text8.Text = CUarray (q)
form1.Text9.Text = GAarray (q)
form1.Text10.Text = GCarray (q)
form1.Text11.Text = GGarray (q)
form1.Text12.Text = GUarray (q)
form1.Text13.Text = UAarray (q)
form1.Text14.Text = UCarray (q)
form1.Text15.Text = UGarray (q)
form1.Text16.Text = UUarray (q)
NNTOTarray(q) = (AAarray(q) + ACarray(q) + AGarray(q) +
AUarray(q) + CCarray(q) + CAarray(q) + CGarray(q) + CUarray(q) +
GGarray(q) + GAarray (q) + GCarray (q) + GUarray (q) + UUarray (q) +
UAarray (q) + UCarray(q) + UGarray(q))
form1.Text18.Text = NNTOTarray(q)
F1 = (UUarray(q))/NNTOTarray(q)
F2 = (AAarray(q))/NNTOTarray(q)
F3 = (GGarray(q))/NNTOTarray(q)
F4 = (CCarray(q))/NNTOTarray(q)
F5 = 2 * (UAarray(q)/NNTOTarray(q))
F6 = 2 * (UGarray (q)/NNTOTarray (q)) − 2 * (GAarray (q)/
NNTOTarray(q)) + 2 * (AGarray(q)/NNTOTarray(q))
F7 = 2 * (CUarray(q))/NNTOTarray(q)
F8 = 2 * (AGarray(q))/NNTOTarray(q)
F9 = 2 * (ACarray(q))/NNTOTarray(q)
F10 = 2 * (GCarray(q))/NNTOTarray(q)
F11 = 3 * (GAarray(q))/NNTOTarray(q) − 3 * (AGarray(q))/
NNTOTarray(q)
F12 = 3 * (CAarray(q))/NNTOTarray(q) − 3 * (ACarray(q))/
NNTOTarray(q)
F13 = 3 * (CGarray(q))/NNTOTarray(q) − 3 * (GCarray(q))/
NNTOTarray(q)
form1.Text17.Text = ((tm1 * F1) + (tm2 * F2) + (tm3 * F3) +
(tm4 * F4) + (tm5 * F5) + (tm6 * F6) + (tm7 * F7) +
(tm8 * F8) + (tm9 * F9) + (rm10 * F10) + (tm11 * F11) +
(tm12 * F12) + (tm13 * F13))
    seekposition = seekposition + 1
    Seek #1, seekposition
position(q) = Val(seekposition − datastart)
form1.Text21.Text = position(q)
Tm(q) = ((tm1 * F1) + (tm2 * F2) + (tm3 * F3) + (tm4 * F4) + (tm5 *
F5) + (tm6 * F6) + (tm7 * F7) + (tm8 * F8) + (tm9 * F9) + (tm10 *
F10) + (tm11 * F11) + (tm12 * F12) + (tm13 * F13))
If form8.Option1.Value = True Then TmEst1(q) = 1/(slope * ((1/
length) − 1/24) + (1/(Tm(q) + 273.15))) Else TmEst1 (q) = Tm(q) +
273.15
    TmEst,(q) = TmEst1(q) − 273.15
GCcontent(q) = (Gccontent(q)/length) * 100
Gcontent(q) = (Gcontent(q)/length) * 100
Ccontent(q) = (Ccontent(q)/length) * 100
form1.Text23.Text = GCcontent(q).
form1.Text24.Text = Gcontent(q)
form1.Text25.Text = Gcontent(q)
q = q + 1
form1.Hscroll1.Value = q
Loop
Close #1
datastart = 0
mrnalength = 0
seekposition = 0
form1.Labe124.Visible = 0
If (Val(form1.Text20.Text) − Val(form1.Text19.Text)) = 0 Then
        form1.Hscroll1.Visible = 0
        form1.Text22.Text = OLIGO(0)
form1.Text17.Text = TmEst(0)
form1.Text23.Text = GCcontent(0)
form1.Text24.Text = Gcontent(0)
form1.Text25.Text = Gcontent(0)
End If
form1.Text22.Visible = 1
form1.Label25.Visible = 1
form1.Text23.Visible = 1
form1.Label26.Visible = 1
form1.Text24.Visible = 1
form1.Label27.Visible = 1
form1.Text25.Visible = 1
form1.Label28.Visible = 1
form8.Option1.Visible = 1
form8.Option1.Visible = 1
form1.Refresh
ending:
Exit Sub
ErrorTrap:
On Error GoTo 0
Close #1
form1.Hscroll1.Visible = 0
form1.Label24.Visible = 0
form6.Show
        Resume ending:
    End Sub
Sub Command2__Click ()
text1.Text = " "
form3.Hide
End Sub
Sub Analyze__Click ()
AA = Val(Text1.Text)
AC = Val(Text2.Text)
AG = Val(Text3.Text)
AU = Val(Text4.Text)
CA = Val(Text5.Text)
CC = Val(Text6.Text)
CG = Val(Text7.Text)
CU = Val(Text8.Text)
GA = Val(Text9.Text)
GC = Val(Text10.Text)
GG = Val(Text11.Text)
GU = Val(Text12.Text)
UA = Val(Text13.Text)
UC = Val(Text14.Text)
UG = Val(Text15.Text)
UU = Val(Text16.Text)
text17 = AA + AC + AG
End Sub
Sub Command1__Click ()
Rem form5.Text1.Text = " "
Rem form5.Show
On Error GoTo errorhandeler:
```

Source Code for Nearest-Neighbor Thermal Stability Analysis

```
CmDialog1.Action = 2
    savename = CmDialog1.Filename
Open savename For Output As #1
Write #1, "position", "Tm", "GC content", "G content", "C content",
"mRNA Target Sequence"
ForH = 0 To q − 1
Write #1, position(H), TmEst(H), GCcontent(H), Gcontent(H),
Content (H), OLIGO(H)
Next H
Close #1
        q = 0
        i = 0
datastart = 0
mrnalength = 0
seekposition = 0
form2.Hide
errorhandeler:
Exit Sub
End Sub
Sub Command2_Click ()
getout = 0
command4.Visible = 1
form7.Show
form7.Refresh
form1.Label28.Visible = 0
form1.Label25.Visible = 0
form1.Text22.Visible = 0
form1.Text23.Visible = 0
form1.Label26.Visible = 0
form1.Text24.Visible = 0
form1.Label27.Visible = 0
form1.Text25.Visible = 0
form1.Label23.Visible = 1
Text1.Text = " "
Text2.Text = " "
Text3.Text = " "
Text4.Text = " "
Text5.Text = " "
Text6.Text = " "
Text7.Text = " "
Text8.Text = " "
Text9.Text = " "
Text10.Text = " "
Text11.Text = " "
Text12.Text = " "
Text13.Text = " "
Text14.Text = " "
Text15.Text = " "
Text16.Text = " "
Text17.Text = " "
Text18.Text = " "
TEXT21.Text = " "
FORM3.Text1.Text = " "
HSCROLL1.Visible = 0
For I = 0 To 3999
    NNTOTarray (i) = 0
    AAarray(i) = 0
    ACarray(i) = 0
    AGarray(i) = 0
    AUarray(i) = 0
    CCarray(i) = 0
    CGarray(i) = 0
    CUarray(i) = 0
    CAarray(i) = 0
    GGarray(i) = 0
    GAarray(i) = 0
    GCarray(i) = 0
    GUarray(i) = 0
    UUarray(i) = 0
    UAarray(i) = 0
    UCarray(i) = 0
    UGarray(i) = 0
    Tm(i) = 0
    TmEst (i) = 0
    TmEst1 (i) = 0
    GCcontent(i) = 0
    Gcontent(i) = 0
    Ccontent(i) = 0
Next i
length = 0
mrnalength = 0
seekposition = 0
datastart = 0
q = 0
Filename = " "
savename = " "
tempname = " "
AA = 0
AC = 0
AG = 0
AU = 0
CA = 0
CC = 0
CG = 0
CU = 0
GG = 0
GA = 0
GU = 0
GC = 0
UU = 0
UC = 0
UA = 0
UG = 0
i = 0
f1 = 0
f2 = 0
f3 = 0
f4 = 0
f5 = 0
f6 = 0
f7 = 0
f8 = 0
f9 = 0
f10 = 0
f11 = 0
f12 = 0
f13 = 0
NNTOT = 0
datastart = 0
    mrnalength = 0
    seekposition = 0
q = 0
H = 0
    form7.Hide
End Sub
Sub Command3_Click ()
If Val(text19.Text) > Val(text20.Text) Then
        form4.Show
        Exit Sub
    Else
If text20.Text = " " Then
        form4.Show
        Exit Sub
    Else
form2.Show
form2.Refresh
Call Command2_Click
End If
    End If
End Sub
Sub Command4_Click ()
End
Unload Me
End Sub
Sub Command5_Click ()
FORM3.Text1.Text = " "
If Val(text19.Text) > Val(text20.Text) Then
        form4.Show
        Exit Sub
    Else
If Val(text19.Text) = 0 Then
        form4.Show
        Exit Sub
    Else
```

Source Code for Nearest-Neighbor Thermal Stability Analysis

```
If text20.Text = " " Then
        form4.Show
        Exit Sub
    Else
Call Command2_Click
FORM3.Show
End If
End If
End If
End Sub
Sub Command6_Click ()
getout = 1
Rem Call Command2_Click
command6.Visible = 0
End Sub
Sub Command7_Click
form8.Show
End Sub
Sub hscroll1_Change ()
TEXT21.Text = HSCROLL1.Value
X = HSCROLL1.Value − 1
If HSCROLL1.Max = 2 Then
    Text22.Text = OLIGO(X)
        form1.Text23.Text = GCcontent (X)
        form1.Text24.Text = Gcontent (X)
        form1.Text25.Text = Ccontent (X)
        Else
text17.Text = TmEst (X)
text18.Text = NNTOTarray (X)
Text23.Text = GCcontent (X)
        form1.Text24.Text = Gcontent (X)
        form1.Text25.Text = Ccontent (X)
        form1.Text1.Text = AAarray (X)
        form1.Text2.Text = ACarray (X)
        form1.Text3.Text = AGarray (X)
        form1.Text4.Text = AUarray (X)
        form1.Text5.Text = CAarray (X)
        form1.Text6.Text = CCarray (X)
        form1.Text7.Text = CGarray (X)
        form1.Text8.Text = Cuarray (X)
        form1.Text9.Text = GAarray (X)
        form1.Text10.Text = GCarray (X)
        form1.Text11.Text = GGarray (X)
        form1.Text12.Text = GUarray (X)
        form1.Text13.Text = UAarray (X)
        form1.Text14.Text = UCarray (X)
        form1.Text15.Text = UGarray (X)
        form1.Text16.Text = UUarray(X)
    Text22.Text = OLIGO(X)
End If
End Sub
Sub Hscroll1-Scroll ()
hscroll1_Change
End Sub
Sub Text1_Change ()
End Sub
Sub Command1_Click ()
On Error GoTo ErrorTrap:
form1.Command4.Visible = 0
form1.Command6.Visible = 1
        form2.Hide
If (Val(form1.Text20.Text) − Val(form1.Text19.Text)) <= 0 Then
    form1.Hscroll1.Max = 1
    form1.Hscroll1.Visible = 0
    Else
    form1.HScroll1.Max = Val(form1.Text20.Text) −
        Val(form1.Text19.Text) + 1
    form1.Hscroll1.Visible = 1
    End If
length = Val(form1.Text19.Text)
form1.Label24.Visible = 1
form1.Label23.Visible = 0
        form1.Refresh
datafile = "data.ini"
Open datafile For Input As #1
Input #1, slope
Input #1, tm1
Input #1, tm2
Input #1, tm3
Input #1, tm4
Input #1, tm5
Input #1, tm6
Input #1, tm7
Input #1, tm8
Input #1, tm9
Input #1, tm10
Input #1, tm11
Input #1, tm12
Input #1, tm13
Close #1
start1:
If Right (file1.Path, 1) # "\" Then
    opFileName = file1.Path & "\" & file1.FileName
    Else
    opFileName = file1.Path & File1.FileName
        End If
mrnalength = 0
seekposition = 0
datastart = 0
q = 0
Open opFileName For Input As #1
headstart:
header = Input$ (1, #1)
If header <> ":" Then
GoTo headstart:
End If
datastart = Seek(1) + 2
mrnalength = Val(form1.Text20.Text)
seekposition = datastart
    Seek #1, seekposition
Do Until seekposition >= mrnalength − length + datastart + 1
i = 0
NN1 = " "
ist = " "
buffer = " "
    OLIGO (q) = Input$ (length, #1)
Seek #1, seekposition
getist:
ist = Input$ (1, #1)
If ist = "a" Then
ist = "A"
End If
If ist = "c" Then
ist = "C"
End If
If ist = "g" Then
ist = "G"
End If
If ist = "u" Then
ist = "U"
End If
If ist = "t" Then
ist = "U"
End If
If ist = "T" Then
ist = "U"
End If
If ist <> "A" And ist <> "G" And ist <> "C" And ist <> "U" Then
    GoTo getist:
    End If
NN1 = ist
    For i = 2 To length
begin:
buffer = Input$ (1, #1)
If buffer = "a" Then
buffer = "A"
End If
If buffer = "c" Then
buffer = "C"
End If
If buffer = "g" Then
buff = "G"
End If
If buffer = "u" Then
```

Source Code for Nearest-Neighbor Thermal Stability Analysis

```
buffer = "U"
End If
If buffer = "t" Then
buffer = "U"
End If
If buffer = "T" Then
buffer = "U"
End If
If ist <> "A" And ist <> "G" And ist <> "C" And ist <> "U" Then
        GoTo begin:
End If
If ist = " " Then GoTo begin:
If ist = Chr (13) Then GoTo begin:
If ist = Chr (10) Then GoTo begin:
continue:
If buffer = "A" Then
If NN1 = "A" Then
        AAarray (q) = AAarray(q) + 1
        End If
If NN1 = "C" Then
        CAarray (q) = CAarray (q) + 1
        End If
    If NN1 = "G" Then
        GAarray (q) = GAaray (q) + 1
        End If
    If NN1 = "U" Then
        UAarray (q) = UAarray (q) + 1
        End If
    NN1 = "A"
    End If
If buffer = "C" Then
    GCcontent (q) = GCcontent (q) + 1
    Ccontent (q) = Ccontent (q) + 1
    If NN1 = "A" Then
        ACarray (q) = ACarray (q) + 1
        End If
    If NN1 = "C" Then
        CCarray(q) = CCarray(q) + 1
        End If
    If NN1 = "G" Then
        GCarray (q) = GCarray (q) + 1
        End If
    If NN1 = "U" Then
        UCarray (q) = Ucarray (q) + 1
        End If
    NN1 = "C"
    End If
If buffer = "G" Then
GCcontent (q) = GCcontent (q) + 1
Gcontent (q) = Gcontent (q) + 1
    If NN1 = "A" Then
        AGarray(q) = AGarray(q) + 1
        End If
    If NN1 = "C" Then
        CGarray(q) = CGarray(q) + 1
        End If
    If NN1 = "G" Then
        GGarray (q) = GGarray (q) + 1
        End If
    If NN1 = "U" Then
        UGarray (q) = UGarray (q) + 1
        End If
NN1 = "G"
End If
■■■■■■■■■■■■■■■■■■■■■■■■■■■■■■■■■■■■■■■■■■■■■
If buffer = "U" Then
    If NN1 = "A" Then
        AUarray (q) = AUarray (q) + 1
        End If
    If NN1 = "C" Then
        CUarray (q) = CUarray (q) + 1
        End If
    If NN1 = "G" Then
        GUarray (q) = GUarray (q) + 1
        End If
    If NN1 = "U" Then
        UUarray (q) = UUarray (q) + 1
        End If
    NN1 = "U"
    End If
Next i
Rem *******last NN pair (imaginary)************
If ist = "A" Then
    If buffer = "A" Then
        AAarray (q) = AAarray (q) + 1
        End If
    If buffer = "C" Then
        CAarray (q) = CAarray (q) + 1
        End If
    If buffer = "G" Then
        GAarray(q) = GAarray (q) + 1
        End If
    If buffer = "U" Then
        UAarray (q) = UAarray (q) + 1
        End If
End If
If ist = "C" Then
    GCcontent (q) = GCcontent(q) + 1
    Ccontent (q) = Ccontent (q) + 1
    If buffer = "A" Then
        ACarray (q) = ACarray(q) + 1
        End If
    If buffer = "C" Then
        CCarray(q) = CCarray(q) + 1
        End If
    If buffer = "G" Then
        GCarray (q) = GCarray (q) + 1
        End If
    If buffer = "U" Then
        UCarray (q) = UCarray (q) + 1
        End If
    End If
If ist = "G" Then
GCcontent (q) = GCcontent (q) + 1
Gcontent (q) = Gcontent (q) + 1
    If buffer = "A" Then
        AGarray (q) = AGarray (q) + 1
        End If
    If buffer = "C" Then
        CGarray (q) = CGarray (q) + 1
        End If
    If buffer = "G" Then
        GGarray (q) GGarray (q) + 1
        End If
    If buffer = "U" Then
        UGarray(q) = UGarray (q) + 1
        End If
    End If
If ist = "U" Then
    If buffer = "A" Then
        AUarray (q) = AUarray (q) + 1
        End If
    If buffer = "C" Then
        CUarray (q) = CUarray (q) + 1
        End If
    If buffer = "G" Then
        GUarray (q) = GUarray (q) + 1
        End If
    If buffer = "U" Then
        UUarray(q) = UUarray(q) + 1
        End If
    End If
form1.Text1.Text = AAarray(q)
form1.Text2.Text = ACarray(q)
form1.Text3.Text = AGarray(q)
form1.Text4.Text = AUarray(q)
form1.Text5.Text = CAarray(q)
form1.Text6.Text = CCarray(q5
form1.Text7.Text = CGarray(q)
form1.Text8.Text = CUarray(q)
form1.Text9.Text = GAarray(q)
form1.Text10.Text = GCarray(q)
form1.Text11.Text = GGarray(q)
form1.Text12.Text = GUarray(q)
```

| Source Code for Nearest-Neighbor Thermal Stability Analysis |
| --- |

```
form1.Text13.Text = UAarray(q)
form1.Text14.Text = UCarray(q)
form1.Text15.Text = UGarray(q)
form1.Text16.Text = UUarray(q)
NNTOTarray(q) = (AAarray(q) + ACarray(q) + AGarray(q) +
AUarray(q) + CCarray(q) + CAarray(q) + CGarray(q) +
CUarray(q) + GGarray(q) + GAarray(q) + Gcarray(q) +
GUarray(q) + UUarray(q) + UAarray(q) + UCarray(q) +
UGarray(q))
form1.Text18.Text = NNTOTarray(q)
F1 = (UUarray(q))/NNTOTarray(q)
F2 = (AAarray(q))/NNTOTarray(q)
F3 = (GGarray(q))/NNTOTarray(q)
F4 = (CCarray(q))/NNTOTarray(q)
F5 = 2 * (UAarray(q)/NNTOTarray(q))
F6 = 2 * (UGarray(q)/NNTOTarray(q)) - 2 * (GAarray(q)/
NNTOTarray(q)) + 2 * (AGarray(q)/NNTOTarray(q))
F7 = 2 * (CUarray(q))/NNTOTarray(q)
F8 = 2 * (AGarray(q))/NNTOTarray(q)
F9 = 2 * (ACarray(q))/NNTOTarray(q)
F10 = 2 * (GCarray(q))/NNTOTarray(q)
F11 = 3 * (GAarray(q))/NNTOTarray(q) - 3 * (AGarray(q))/
NNTOTarray(q)
F12 = 3 * (CAarray(q))/NNTOTarray(q) - 3 * (ACarray(q))/
NNTOTarray(q)
F13 = 3 * (CGarray(q))/NNTOTarray(q) - 3 * (GCarray(q))/
NNTOTarray(q)
form1.Text17.Text = ((tm1 * F1) + (tm2 * F2) + (tm3 * F3) +
(tm4 * F4) + (tm5 * F5) + (tm6 * F6) + (tm7 * F7) +
(tm8 * F8) + (tm9 * F9) + (tm10 * F10) + (tm11 * F11) +
(tm12 * F12) + (tm13 * F13))
    seekposition = seekposition + 1
    Seek #1, seekposition
position(q) = Val(seekposition - datastart)
form1.Text21.Text = position(q)
Tm(q) = ((tm1 * F1) + (tm2 * F2) + (tm3 * F3) + (tm4 * F4) + (tm5 *
F5) + (tm6 * F6) + (tm7 * F7) + (tm8 * F8) + (tm9 * F9) +
(tm10 * F10) + (tm11 * F11) + (tm12 * F12) + (tm13 * F13))
If form8.Option1.Value = True Then TmEst1(q) = 1/(slope * ((1/length) -
1/24) + (1/(Tm(q) + 273.15))) Else TmEst1(q) = Tm(q) + 273.15
TmEst(q) = TmEst1(q) - 273.15
GCcontent(q) = (GCcontent(q)/length) * 100
Gcontent(q) = (Gcontent(q)/length) * 100
Ccontent(q) = (Ccontent(q)/length) * 100
form1.Text23.Text = GCcontent(q)
form1.Text24.Text = Gcontent(q)
form1.Text25.Text = Gcontent(q)
    q = q + 1
    form1.Hscroll1.Value = q
    DoEvents
If getout = 1 Then
    GoTo loopout:
        End If
Loop
loopout:
Close #1
datastart = 0
mrnalength = 0
seekposition = 0
form1.Label24.Visible = 0
If (Val(form1.Text20.Text) - Val(form1.Text19.Text)) = 0 Then
    form1.Hscroll1.Visible = 0
    form1.Text22.Text = OLIGO(0)
    form1.Text17.Text = TmEst(0)
    form1.Text23.Text = GCcontent(0)
    form1.Text24.Text = Gcontent(0)
    form1.Text25.Text = Ccontent(0)
        End If
form1.Text22.Visible = 1
form1.Label25.Visible = 1
form1.Text23.Visible = 1
form1.Label26.Visible = 1
form1.Text24.Visible = 1
form1.Label27.Visible = 1
form1.Text25.Visible = 1
form1.Label28.Visible = 1
form1.Label23.Visible = 1
form1.Command6.Visible = 0
form1.Command4.Visible = 1
form1.Refresh
ending:
Exit Sub
ErrorTrap:
On Error GoTo 0
    Close #1
    form1.HScroll1.Visible = 0
    form1.Label24.Visible = 0
    form6.Show
    form1.Command6.Visible = 0
    form1.Command4.Visible = 1
    form1.Refresh
    Resume ending:
End Sub
Sub Command2_Click ()
form2.Hide
End Sub
Sub Dir1_Change ()
file1.Path = dir1.Path
End Sub
Sub Drive1_Change ()
start:
    On Error GoTo EH
    dir1.Path = drive1.Drive
    Exit Sub
    EH:
    drive1 = "c:\"
    On Error GoTo 0
    Resume start:
    End Sub
Sub File1_DblClick ()
    Call Command1_Click
    End Sub
    Sub Form_Load ()
    If Val(form1.Text19.Text) = Val(form1.Text20.Text) Then
        form1.HScroll1.Visible = 0
    Else
        form1.HScroll1.Visible = 1
        form1.Refresh
End If
End Sub
Sub Command1_Click ()
form8.Hide
End Sub
Sub Command1_Click ()
savename = Text1.Text
If savename = "abort" Then
GoTo ending:
End If
Open savename For Output As #1
Write #1, "position", "Tm", "GC content", "G content", "C content",
"in RNA Target"
For H = 0 To q - 1
Write #1, position(H), TmEst(H), GCcontent(H), Gcontent(H),
Ccontent(H), OLIGO(H)
Next H
Close #1
q = 0
i = 0
datastart = 0
mrnalength = 0
seekposition = 0
form2.Hide
ending:
form5.Hide
End Sub
Sub Command2_Click ()
Text1.Text = "abort"
form5.Hide
End Sub
Global opFileName As String
Global savename As String
Global tempname As String
Global oligo(4000)
Global TmEst(4000)
```

-continued

Source Code for Nearest-Neighbor Thermal Stability Analysis

Global TmEst1(4000)
Global slope
Global GCcontent(4000)
Global Gcontent(4000)
Global Ccontent(4000)
Global getout
Global AA
Global AC
Global AG
Global AU
Global CC
Global CA
Global CG
Global CU
Global GG
Global GA
Global GC
Global GU
Global UU
Global UA
Global UC
Global UG
Global AAarray(4000)
Global ACarray(4000)
Global AGarray(4000)
Global AUarray(4000)
Global GAarray(4000)
Global GUarray(4000)
Global GCarray(4000)
Global GGarray(4000)
Global UUarray(4000)
Global UGarray(4000)
Global UCarray(4000)
Global UAarray(4000)
Global CAarray(4000)
Global CUarray(4000)
Global CGarray(4000)
Global CCarray(4000)
Global NNTOTarray(4000)
Global f1
Global f2
Global f3
Global f4
Global f5
Global f6
Global f7
Global f8
Global f9
Global f10
Global f11
Global f12
Global f13
Global length
Global position(4000)
Global tm(4000)
Global datastart
Global mrnalangth
Global seekposition
Global q
Global h The present invention may be carried out in other specific ways other than those set forth herein without parting from the spirit and essential characteristics and scope of the present invention. The present embodiments set forth above are to be considered in all respects as illustrative and non-restrictive and all changes coming within the equivalency range of the appended claims are intended to be embraced within this invention.

REFERENCES

Agrawal, S. et al., *Proc. Natl. Acad. Sci. USA.*, 85:7079–7083, 1988.

Agrawal, S. et al., *Proc. Natl. Acad. Sci. U.S.A.*, 86:7790–7794, 1989.

Bennett, C. F. et al., "Inhibition of Endothelial Adhesion Molecule Expression with Antisense Oligonucleotides, *J. of Immunology*, 152:3530–3540, 1994.

Bernstein, P., "Start Making Antisense," Research Brief in *Nature Biotechnology* 16:10 (1998).

Buck, H. M., et al., *Science*, 248:208–212, 1990.

Cantor, C. R., et al., "Biophysical Chemistry Part III," Freeman, W. H., San Francisco, pp. 1187–1190, 1980.

Cavenave, C., et al., *Nuc. Acids Res.*, 17:4255–4273, 1989.

Chiang, M.-Y., et al., "Antisense Oligonucleotides Inhibit Intercellular Adhesion Molecule I Expression by Two Distinct Mechanisms," *J. Biol. Chem.*, 266:18162–18171, 1991.

Cohen, J. S., "Oligonucleotides—Antisense Inhibitors of Gene Expression," CRC Press, Boca Raton, Fla., 1989.

Cory, D. R. and Schultz, P. G., *Science*, 238:1401–1403, 1987.

Eckstein, F., *Anal Biochem.* 54:367–402, 1985.

Freier, S. M., et al., *Thermodynamics of Antisense Oligonucleoide Hybridization* in "Gene Regulation: Biology of Antisense RNA and DNA" (Eds. Erickson, R. P. & Izant, J. G.) pp. 95–107, Raven Press, Ltd., New York, 1992.

Goldstein, R. F. and Benight, A. S., "How Many Numbers are Required to Specify-Sequence Dependent Properties of Polynucleotides?" *Biopolymers*, 42:795–810, 1992.

Goodchild, S., et al., *Proc. Natl. Acad. Sci. U.S.A.*, 859:5507–5511, 1988.

Gray, D. M., "Derivation of nearest-neighbor properties from data on nucleic acid oligomers. I. Simple sets of independent sequences and the influence of absent nearest neighbors," *Biopolymers*, 42:783–793, 1997a.

Gray, D. M., "Derivation of nearest-neighbor properties from data on nucleic acid oligomers. II.Thermodynamic parameters of DNA•RNA hybrids and DNA duplexes," *Biopolymers*, 42:795–810, 1997b.

Gray, D. M. and Tinoco, Jr., I., "A New Approach to the Study of Sequence-Dependent Properties of Polynucleotides," *Biopolymers*, 9:223–244, 1970.

Gray, G. D., et al., *Biochem. Pharmacol.* 53:1465–1476, 1997.

Hashem, G. M., et al. "Hybrid Oligomer Duplexes Fored with Phosphorothroate DNAs: CD Spectra and Melting Temperatures of S-DNA:RNA Hybrids are Sequence-Dependent but Consistent with Similar Heteronomous Conformations," *Biochemistry*, 37:61–72, 1998.

Hung, S. H., et al., "Evidence from CD Spectra that d(purine): r(pyrimidine) and r(purine): (pyrimidine) Hybrids are in Different Structural Classes," *Nucl. Acids Res.*, 22:4326–4334, 1994.

Kiessling, L. L., et al., "Flanking Sequence Effects within the Pyrimidine Triple-Helix Motif Characterized by Affinity Clearing," *Biochemistry*, 31:2829–2834.

Laughton, D. A., and Neidle, S., "Prediction of the Structure of the Y+:R−: R+Type DNA Triple Helix by Molecular Modeling," *Nucl. Acids Res.*, 20:6535–6541, 1992

Lesnik, E. A. and Freier, S. M., "Relative Thermodynamic Stability of DNA, RNA, and DNA:RNA Hybrid Duplexes: Relationship with Base Composition and Structure," *Biochemistry*, 35:10807–10815, 1995.

Letsinger, R. L., et al., "*Proc. Natl. Acad. Sci. U.S.A.*, 86:6553–6556, 1989.

Lisziewicz, J., et al., "Antisense Oligodeoxynucleotide Phosphorothioate Complementary to Gag mRNA Blocks Replication of Human Immunodeficiency Virus Type I in Human Peripheral Blood Cells," *Proc. Natl. Acad. Sci. U.S.A.*, 91:7942–7946, 1994.

Marcus-Sekura, C. J., *Anal. Biochem*, 172:289–295, 1988.

Matsukura, M., et al., *Proc. Natl. Acad. Sci. U.S.A.*, 84:7706–7710, 1987.

Matsukura, M., et al., *Gene*, 72:343–347, 1988.

Matteucci, M. D. and Wagner, R. W., "In pursuit of Antisense," *Nature*, 384:20–22, 1996.

Melton, D. A. (Ed.) "Antisense RNA and DNA," Cold Spring Harbor Press, Cold Spring Harber, 1988.

Mercola, D. and Cohen, J. S., *Cancer Gene Therapy*, 2:47–59, 1995.

Mori, K., et al., *Nucl. Acids Res.*, 17:8207–8219, 1989.

Pilch, D. S., et al., "Structure, Stability, and Thermodynamics of a Short Intermolecular Purine-Purine-Pyrimidine Triple Helix," *Biochemistry*, 30:6081–6087, 1991.

Press, W. H., et al., "Numerical Recipes in C, the Art of Scientific Computing," $2^{nd}$ edition, (pp. 59–70, Cambridge University Press, Cambridge, England), 1992.

Ratmeyer, L., et al., "Sequence Specific Thermodynamic and Structural Properties for DNA:RNA duplexes," *Biochemistry*, 33:5298–5304, 1994.

Sarin, P. S., et al., *Proc. Natl. Adac. Sci. US.A.*, 85:7448–7451, 1988.

Shibahara, S., et al., *Nucl. Acids Res.*, 17:239–252, 1989.

Stein, C. A. and Chen, Y.-C., "Antisense Oligonucleotides as Therapeutic Agents—Is the Bullett Really Magical?" *Science*, 261:1004–1012, 1993.

Stein, C. A., and Cohen, J. S., "Oligodeoxynucleotides as Inhibitors of Gene Expression; A Review," *Cancer Research*, 48:2659–2668, 1988.

Stevenson, M., and Iversen, P. L., *J. Gen. Virol.*, 70:2673–2682, 1989.

Stull, R. A., et al., "Predicting Antisense Oligonucleotide Inhibitory Efficacy: A Computational Approach Using Histograms and Thermodynamic Indices," *Nucl. Acids Res.*, 20:3501–3508, 1992.

Sugimoto, N., et al., "Thermodynamic Parameters to Predict Stability of RNA/DNA Hybrid Duplexes," *Biochemistry*, 34:11211–11216, 1995.

Toulmé, J. -J. and Hélène, C., "Antimessenger Oligodeoxynucleotides: An Alternative to Antisense RNA for Artificial Regulation of Gene Expression—A Review," *Gene*, 72:51–58, 1988.

Van der Krol, A. R., et al., *BioTechniques*, 6:958–973, 1988.

Walder, J., *Genes & Development*, 2:502–504, 1988.

Walder, R. T. and Walder, J. A., *Proc. Natl. Acad. Sci U.S.A.*, 85:5011–5015, 1988.

Zaia, J. A., et al., *J. Virol.*, 62:3914, 1988.

Zamecnik, P. et al., *Proc. Natl. Acad. Sci. US.A.*, 83:4143–4146, 1986.

Zamecnik, P. and Stephenson, M., *Proc. Natl. Acad. Sci. US.A.*, 75:280–284, 1978.

Zon, G., *Pharmaceutical Research*, 5:539–549, 1988.

---

What is claimed is:

1. A method for identifying a nucleic acid molecule having a sequence capable of targeting a gene of interest comprising:

(a) a first database comprising a list of stability values for independent combinations of nearest-neighbor nucleic acid base pairs;

(b) a computing unit comprising:
      a means for inputting data comprising a nearest-neighbor nucleic acid pair, N(x), data list, defining a nucleic acid sequence of interest to be targeted to provide a second database; and (c) a program capable of processing said first and said second database to provide a nearest-neighbor nucleic acid base pair, N(x), comparison and provide a stability value of a nucleic acid sequence capable of targeting the gene of interest.

2. The method of claim 1, wherein, for a U:A pair, said nearest-neighbor nucleic acid base pair, N(x), is constrained by the formula N(1)+N(2)+N(3)+N(4)=N(2)+N(6)+N(10)+N(14), wherein N is the number of occurrences of that nearest-neighbor base pair in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
|---|---|---|---|
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

3. The method of claim 1, wherein, for an A:T pair, said nearest-neighbor nucleic acid base pair, N(x), is constrained by the formula N(5)+N(6)+N(7)+N(8)=N(1)+N(5)+N(9)+N(13), wherein N is the number of occurrences of that nearest-neighbor in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
|---|---|---|---|
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

4. The method of claim 1, wherein, for a C:G pair, said nearest-neighbor nucleic acid base pair, N(x), is constrained by the formula N(9)+N(10)+N(11)+N(12)=N(3)+N(7)+N(11)+N(15), wherein N is the number of occurrences of that nearest-neighbor in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
|---|---|---|---|
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

5. The method of claim 1, wherein identifying nucleic acid sequences for antisense oligonucleotide targeting further comprises the steps of:
   determining the fractions of a nearest-neighbor base pair in each target sequence zone RNA:ASO-DNA hybrid sequence;
   substituting nearest-neighbor nucleic acid base pair fractions into formulas to determine the fractions of each of a series of 13 independent nearest-neighbor base pair combinations;

adding the products of the fractions which have been multiplied by the stability values of the independent combinations to determine a hybrid stability value for each target sequence zone RNA:DNA hybrid sequence.

6. The method of claim 5, wherein said hybrid duplex stability value is used to determine the relative stability of the DNA:RNA hybrid.

7. The method of claim 1, wherein the means for displaying the input data defining the nucleic acid sequence is a computer screen.

8. The method of claim 1, further comprising a means for displaying the input data defining the nucleic acid sequence.

9. The method of claim 1, wherein the means for displaying the input data is a printer.

10. The method of claim 1, wherein said computing unit further comprises a means capable of recording said hybrid stability values to a tangible recording medium.

11. The method of claim 1, wherein said means for inputting data is a keyboard.

12. The method of claim 1, wherein said means for inputting data is a memory device.

13. The method of claim 1, wherein said means for inputting data is a modem.

14. The method of claim 1, wherein said computing unit further performs the function of accepting a nucleic acid segment length value wherein said comparison of said nucleic acid nearest-neighbor nucleic acid pair value data list further includes comparing each nucleic acid segment of said length within said nucleic acid sequence with said list of stability values for independent combinations of nearest-neighbor nucleic acid base pairs.

15. A method for identifying nucleic acid sequences for antisense oligonucleotide targeting comprising the steps of:
    storing a plurality of operating instructions in a memory unit of a control computer; and
    operating said control computer pursuant to said plurality of operating instructions for:
        accessing a list of values for independent combinations of nearest-neighbor nucleic acid base pairs;
        obtaining a nucleic acid sequence;
        accepting a nucleic acid segment length value;
        comparing each nucleic acid segment within said nucleic acid sequence with said list of values for independent combinations of nearest-neighbor nucleic acid base pairs; and
        identifying nucleic acid sequences for antisense oligonucleotide targeting by determining a hybrid duplex stability value for each contiguous nucleic acid segment of said length within said nucleic acid sequence.

16. The method of claim 15, wherein, for a U:A pair, said nearest-neighbor nucleic acid base pair, N(x), is constrained by the formula $N(1)+N(2)+N(3)+N(4)=N(2)+N(6)+N(10)+N(14)$, wherein N is the number of occurrences of that nearest-neighbor base pair in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
|---|---|---|---|
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

17. The method of claim 15, wherein, for a A:T pair, said nearest-neighbor nucleic acid base pair, N(x), is constrained by the formula $N(5)+N(6)+N(7)+N(8)=N(1)+N(5)+N(9)+N(13)$, wherein N is the number of occurrences of that nearest-neighbor in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
|---|---|---|---|
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

18. The method of claim 15, wherein, for a C:G pair, said nearest-neighbor nucleic acid pair base pair, N(x), is constrained by the formula $N(9)+N(10)+N(11)+N(12)=N(3)+N(7)+N(11)+N(15)$, wherein N is the number of occurrences of that nearest-neighbor in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
|---|---|---|---|
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

19. The method of claim 15, further comprising the step of ranking said hybrid duplex stability value for each nucleic acid segment of said length of said nucleic acid sequence in descending order.

20. A compiler for identifying nucleic acid sequences for antisense oligonucleotide targeting comprising:
    a first plurality of binary values for obtaining a nucleic acid sequence in a first data format;
    a second plurality of binary values containing a list of stability values for independent combinations of nearest-neighbor nucleic acid base pairs in a second data format;
    a third plurality of binary values for comparing said nucleic acid sequence with said list of stability values for independent combinations of nearest-neighbor nucleic acid base pairs, N(x), to obtain hybrid duplex stability values; and
    a fourth plurality of binary values for electronically routing said hybrid duplex stability values to an output device.

21. The compiler of claim 20, wherein, for a U:A pair, said nearest-neighbor nucleic acid base pair, N(x), is constrained by the formula $N(1)+N(2)+N(3)+N(4)=N(2)+N(6)+N(10)+N(14)$, wherein N is the number of occurrences of that nearest-neighbor in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
|---|---|---|---|

-continued

| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

22. The compiler of claim 20, wherein, for an A:T pair, said nearest neighbor nucleic acid base pair N(x), is constrained by the formula N(5)+N(6)+N(7)+N(8)=N(1)+N(5)+N(9)+N(13), wherein N is the number of occurrences of that nearest-neighbor in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

23. The compiler of claim 20, wherein, for a C:G pair, said nearest-neighbor nucleic acid base pair, N(x) is constrained by the formula N(9)+N(10)+N(11)+N(12)=N(3)+N(7)+N(11)+N(15), wherein N is the number of occurrences of that nearest-neighbor type in a sequence, and x is the numerical label of a nearest-neighbor base pair in DNA:RNA hybrids selected from the group consisting of:

| 1 (U-A) (A-T); | 2 (U-U) (A-A); | 3 (U-C) (A-G); | 4 (U-G) (A-C); |
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

24. A method for selectively ranking antisense oligonucleotides for inhibitory efficiency comprising the steps of:
  determining the fractions of nearest-neighbor base pair types in each target sequence zone RNA:ASO-DNA hybrid sequence;
  substituting nearest-neighbor base pair fractions into formulas to determine the fractions of each of a series of 13 independent nearest-neighbor base pair combinations; and
  determining a hybrid duplex stability value for each target sequence zone RNA:DNA hybrid sequence wherein the duplex stability values for said target sequence zones are ordered to produce a ranking for inhibitory efficiency.

25. The method of claim 24, wherein, for a U:A pair, said nearest-neighbor nucleic acid base pair, N(x), is constrained by the formula N(1)+N(2)+N(3)+N(4)=N(2)+N(6)+N(10)+N(14), wherein N is the number of occurrences of that nearest-neighbor base in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

26. The method of claim 24, wherein, for an A:T pair, said nearest-neighbor nucleic acid base pair, N(x), is constrained by the formula N(5)+N(6)+N(7)+N(8)=N(1)+N(5)+N(9)+N(13), wherein N is the number of occurrences of that nearest-neighbor base pair in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

27. The method of claim 24, wherein, for a C:G pair, said nearest-neighbor neighbor nucleic acid base pair, N(x), is constrained by the formula N(9)+N(10)+N(11)+N(12)=N(3)+N(7)+N(11)+N(15), wherein N is the number of occurrences of that nearest-neighbor base pair in a sequence, and x is a numerical label of a nearest-neighbor base pair in a DNA:RNA hybrid selected from the group consisting of:

| 1 (U-A) (A-T); | 2 (U-U) (A-A); | 3 (U-C) (A-G); | 4 (U-G) (A-C); |
| 5 (A-A) (T-T); | 6 (A-U) (T-A); | 7 (A-C) (T-G); | 8 (A-G) (T-C); |
| 9 (C-A) (G-T); | 10 (C-U) (G-A); | 11 (C-C) (G-G); | 12 (C-G) (G-C); |
| 13 (G-A) (C-T); | 14 (G-U) (C-A); | 15 (G-C) (C-G); and | 16 (G-G) (C-C). |

28. The method of claim 24, wherein said hybrid duplex stability ranking value for the target sequence zone RNA:ASO-DNA hybrid sequence is determined by multiplying the fractions of the 13 independent nearest-neighbor base pair combinations by the stability values of the combinations and adding the products.

29. The method of claim 23, further comprising the step of comparing the stability values for various target sequence zones to assess the relative ranking of a specific target sequence zone RNA:ASO-DNA hybrid nucleic acid sequence.

30. A method for selectively ranking antisense oligonucleotides for hybridization efficiency comprising the steps of:
  determining the fractions of nearest-neighbor base pair types in each target sequence zone RNA:ASO-DNA hybrid sequence;
  substituting nearest-neighbor nucleic acid base pair fractions into formulas to determine the fractions of each of a series of 13 independent nearest-neighbor base pair combinations; and
  adding the products of the fractions which have been multiplied by the stability values of the independent combination to determine a hybrid stability value for each target sequence zone;

wherein the stability values for said target sequence zones are ordered to produce a ranking for hybridization efficiency.

31. A method for selectively ranking an antigene oligonucleotide sequence for inhibitory efficiency comprising the steps of:

determining the fractions of nearest-neighbor base triplet types in each target sequence zone DNA:AGO-DNA triplex sequence;

substituting nearest-neighbor triplet fractions into formulas to determine the fractions of each of three independent nearest-neighbor combinations of nucleic acid sequence triplet types selected from the group consisting of: poly[d(T):d(A):d(T)]; poly[d(C+):d(G):d(C)]; and poly[d(TC+):d(AG):d(CT)]; and multiplying the fractions of the independent nearest-neighbor triplet combinations by the stability values of the combinations and adding the products to give a triplex stability ranking value for the target sequence zone DNA:AGO-DNA triplex nucleic acid sequence; wherein the results for various target sequence zone DNA sequences are ordered to produce a ranking for inhibitory efficiency.

32. The method of claim 31, wherein said step of substituting nearest-neighbor triplet fractions into formulas comprises substitution into formulas to determine the fractions of each of seven independent nearest-neighbor combinations of nucleic acid sequence triplet types selected from a group consisting of: poly[d(A):d(A):d(T)]; poly[d(T):d(A):d(T)]; poly[d(G):d(G):d(C)]; poly[d(AT):d(AA):d(TT)]; poly[d(AG):d(GA):d(TC)]; poly[d(GT):d(AG):d(CT)]; and poly[d(ATG):d(GAA):d(TTC)].

33. The method of claim 31, wherein a triplex stability ranking value for the target sequence zone DNA:AGO-DNA triplex formed is determined by adding the totals of determined fractions of independent combinations that have been multiplied by stability values of such combinations.

34. The method of claim 31, further comprising the step of comparing the ranking values for various target sequence zones to assess the relative stability of a specific target sequence zone DNA:AGO-DNA triplex nucleic acid sequence.

35. A method for ranking an antigene oligonucleotide sequence for hybridization efficiency comprising the steps of:

determining the fractions of nearest-neighbor base triplet types in each target sequence zone DNA:AGO-DNA triplex sequence;

substituting nearest-neighbor triplet fractions into formulas to determine the fractions of each of three independent nearest-neighbor combinations of nucleic acid sequence triplet types selected from the group consisting of: poly[d(T):d(A):d(T)]; poly[d(C+):d(G):d(C)]; and poly[d(TC+):d(AG):d(CT)]; and multiplying the fractions of the independent nearest-neighbor triplet combinations by the stability values of the combinations and adding the products to give a triplex stability ranking value for the target sequence zone DNA:AGO-DNA triplex nucleic acid sequence; wherein the results for various target sequences zone DNA sequences are ordered to produce a ranking for hybridization efficiency of said antigene oligonucleotide.

36. The method of claim 35, wherein said step of substituting nearest-neighbor triplet fractions into formulas comprises substitution into formulas to determine the fractions of each of seven independent nearest-neighbor combinations of nucleic acid triplet types selected from the group consisting of: poly[d(A):d(A):d(T)]; poly[d(T):d(A):d(T)]; poly[d(G):d(G):d(C)]; poly[d(AT):d(AA):d(TT)]; poly[d(AG):d(GA):d(TC)]; poly[d(GT):d(AG):d(CT)]; and poly[d(ATG):d(GAA):d(TTC)].

37. The method of claim 35, wherein a triplex stability ranking value for the target sequence zone DNA:AGO-DNA triplex formed is determined by adding the totals of determined fractions of independent combinations that have been multiplied by stability values of such combinations.

38. The method of claim 35, further comprising the step of comparing the ranking values for various target sequence zones to assess the relative stability of a specific target sequence zone DNA:AGO-DNA triplex nucleic acid sequence.

39. A method for controlling gene expression by selectively locating a target sequence zone comprising the steps of:

obtaining a target sequence;

determining the fractions of nearest-neighbor base pair or base triplet types in each subsequence target sequence zone within said target sequence;

substituting nearest-neighbor nucleic acid base pair or base triplet fractions into formulas to determine the fractions of each of a series of independent nearest-neighbor base pair combinations;

determining a duplex or triplex stability value by multiplying the fractions by the stability values of the independent combinations and adding the products;

eliminating one or more subsequence target sequence zones from all possible subsequence target zones; and ordering the remaining stability values to produce a ranking of the remaining subsequence target sequence zones for efficiency of controlling gene expression.

40. A method for identifying nucleic acid sequences for antisense oligonucleotide targeting by selectively locating a target sequence zone comprising the steps of:

obtaining a target sequence;

determining the fractions of nearest-neighbor base pair and base pair-plus-end neighbor types in each subsequence target sequence zone of any length within said target sequence;

substituting fractions of nucleic acid nearest-neighbor base pair or base pair-plus-end neighbor types into formulas to determine the fractions of each of a series of 20 independent nearest-neighbor combinations which take end effects into account selected from the group consisting of: EUAE/ETAE, EUUE/EAAE, EUCE/EGAE, EUGE/ECAE, EAAE/ETTE, EAUE/EATE, EACE/EGTE, EAGE/ECTE, ECAE/ETGE, ECUE/EAGE, ECCE/EGGE, ECGE/ECGE, EGAE/ETCE, EGUE/EACE, EGCE/EGCE, EGGE/ECCE, EUE/EAE, EAE/ETE, and ECE/EGE, EGE/ECE: determining a hybrid stability value for each subsequence target zone by multiplying the fractions by the stability values of the 20 independent nearest-neighbor combinations and adding the products;

eliminating one or more subsequence target sequence zones from the possible subsequence target sequence zones; and ordering the remaining stability values to produce a ranking of the remaining subsequence target sequence zones to provide nucleic acid sequences for antisense oligonucleotide targeting.

* * * * *

UNITED STATES PATENT AND TRADEMARK OFFICE
CERTIFICATE OF CORRECTION

PATENT NO. : 6,183,966 B1  
DATED : February 6, 2001  
INVENTOR(S) : Donald M. Gray et al.

Page 1 of 3

It is certified that error appears in the above-identified patent and that said Letters Patent is hereby corrected as shown below:

Title page,
References Cited, delete "Kiessling, L.L., et al., "Flanking Sequence Effects within the Pyrimidine Triple-Helix Motif Characterized by Affinity Clearing," *Biochemistry*, 31:2829-2834", add -- Kiessling, L.L., et al., "Flanking Sequence Effects within the Pyrimidine Triple-Helix Motif Characterized by Affinity Clearing," *Biochemistry*, 31:2829-2834, 1992. --.

Column 8,
Line 20, delete "pp.22-23", insert -- columns 14-15 --.
Line 28, after "HYBsimulator", delete "used", insert -- referred to --.
Line 37, delete "pp.24-25", insert -- column 16, equations 1, 2 and 3 --.

Column 10,
Line 31, delete "αG", insert -- ΔG --.
Line 32, delete "αG", insert -- ΔG --.

Column 15,
Line 45, above "r(AG):r(CU)", insert heading -- RNA:RNA Duplex --.
Line 49, above "d(AG):r(CU)", delete "DNA:DNA Hybrid", insert -- DNA:RNA Hybrid --.
Line 53, above "r(AG):d(CT)", insert heading -- RNA-DNA Hybrid --

Column 19,
Line 13, delete "Tm (r(ACU):S-d(AGT)$_8$)", insert -- Tm ( r(ACU)$_8$:S-d(AGT)$_8$) --.
Line 18, delete "52.4", insert -- 52.2 --.

Column 22,
Table 8, delete "f (Dtc)", insert -- f(dTC) --.

Column 32,
Line 29, table 16, below "Example sets of independent triplex DNA:DNA:DNA.", delete duplicate line "Example sets of independent triplex DNA:DNA:DNA."

UNITED STATES PATENT AND TRADEMARK OFFICE
CERTIFICATE OF CORRECTION

PATENT NO.   : 6,183,966 B1
DATED        : February 6, 2001
INVENTOR(S)  : Donald M. Gray et al.

It is certified that error appears in the above-identified patent and that said Letters Patent is hereby corrected as shown below:

Column 33,
Line 4, table 16, below "Example sets of independent triplex DNA:DNA:DNA.", delete duplicate line "Example sets of independent triplex DNA:DNA:DNA."

Column 37,
Line 22, delete "-9.5° 10 kcal/mol", insert -- -9.5 kcal/mol --.

Column 40,
Line 57, after "Print #1;", delete " ", insert -- ":" --.
Line 61, after "header < >", delete " ", insert -- ":" --.

Column 41,
Line 5, delete "mmalength", insert -- mrnalength --.

Column 47,
Line 36, delete "Cuarray (X)", insert -- CUarray (X) --.

Column 49,
Line 56, delete black line "▫▫▫▫▫▫▫▫▫▫▫▫▫▫▫".

Column 51,
Line 10, delete "Gcarray (q)", insert -- GCarray (q) --.

Column 52,
Line 48, delete "in RNA target", insert -- in mRNA target --.

Column 53,
Line 50, delete "Global mrnalangth", insert -- Global mrnalength --.
At the end of the Source Code, below "Global h", insert -- Global ist As String --.

Column 54,
Line 52, after "2829-2834", insert -- , 1992. --.

Column 72,
Line 30, after "nearest-neighbor", delete "neighbor".

UNITED STATES PATENT AND TRADEMARK OFFICE
CERTIFICATE OF CORRECTION

PATENT NO. : 6,183,966 B1
DATED : February 6, 2001
INVENTOR(S) : Donald M. Gray et al.

It is certified that error appears in the above-identified patent and that said Letters Patent is hereby corrected as shown below:

Drawings,
In the top half of Figure 5, after "CALCULATED MELTING TEMPERATURE (DEG. C)", delete "mRNAL LENGTH", insert -- mRNA LENGTH --.

Signed and Sealed this

Twenty-third Day of April, 2002

Attest:

Attesting Officer

JAMES E. ROGAN
Director of the United States Patent and Trademark Office

SEQUENCE LISTING

<160> NUMBER OF SEQ ID NOS: 38

<210> SEQ ID NO 1
<211> LENGTH: 27
<212> TYPE: RNA
<213> ORGANISM: Artificial Sequence
<220> FEATURE:
<223> OTHER INFORMATION: Description of Artificial Sequence:
      Theoretical mRNA

<400> SEQUENCE: 1
acgggccucu cuugcaaggg cuaaggu                                          27

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: ASO

<400> SEQUENCE: 2
agaggcccgt                                                             10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: ASO

<400> SEQUENCE: 3
gagaggcccg                                                             10

<210> SEQ ID NO 4
<211> LENGTH: 10
<212> TYPE: DNA
<213> ORGANISM: Artificial Sequence
<220> FEATURE:

```
<223> OTHER INFORMATION: Description of Artificial Sequence: ASO

<400> SEQUENCE: 4
agagaggccc                                                              10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: ASO

<400> SEQUENCE: 5
aagagaggcc                                                              10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: ASO

<400> SEQUENCE: 6
caagagaggc                                                              10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: ASO

<400> SEQUENCE: 7
gcaagagagg                                                              10

<210> SEQ ID NO 8
<211> LENGTH: 24
<212> TYPE: RNA
<213> ORGANISM: Artificial Sequence
<220> FEATURE:
<223> OTHER INFORMATION: Description of Artificial Sequence: Hybrid mRNA

<400> SEQUENCE: 8
agagagagag agagagagag agag                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Hybrid DNA

<400> SEQUENCE: 9
ctctctctct ctctctctct ctct                                              24

<210> SEQ ID NO 10
<211> LENGTH: 24
<212> TYPE: RNA
<213> ORGANISM: Artificial Sequence
<220> FEATURE:
<223> OTHER INFORMATION: Description of Artificial Sequence: Hybrid mRNA

<400> SEQUENCE: 10
ucucucucuc ucucucucuc ucuc                                              24
```

```
<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Hybrid DNA

<400> SEQUENCE: 11
gagagagaga gagagagaga gaga                                              24

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: ASO

<400> SEQUENCE: 12
cccccaccac ttcccctctc                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 13
tgcccatcag ggcagtttga                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 14
cctgtcccgg gataggttca                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 15
cccccaccac ttcccctctc                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 16
gcccaagctg gcatccgtca                                                   20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: S-ASO
```

```
<400> SEQUENCE: 17
gacactcaat aaatagctgg t                                              21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 18
ttgagaaagc tttattaact                                                20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 19
ggctccattt cttgctctcc                                                20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 20
catttcttgc tctcctctgt                                                20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 21
gctatgtcga cacccaattc                                                20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 22
ccgcccctcg cctcttgccg                                                20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 23
cgggtcccct cgggattggg                                                20

<210> SEQ ID NO 24
<211> LENGTH: 20
```

```
<212> TYPE: DNA
<213> ORGANISM: Artificial Sequence
<220> FEATURE:
<223> OTHER INFORMATION: Description of Artificial Sequence: S-ASO

<400> SEQUENCE: 24
cgggtcccct cgggattggg                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 25
caccttcttc ttctattcct                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 26
gaagtcagcc aagaacagct                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 27
tataggagtt ttgatgtgaa                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 28
ctgctgcctc tgtctcaggt                                               20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 29
acaggatctc tcaggtgggt                                               20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: S-ASO

<400> SEQUENCE: 30
```

```
aatcatgact tcaagagttc t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: S-ASO

<400> SEQUENCE: 31
tgaagcaatc atgacttcaa g                                              21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 32
ccaaagtgag agctgagaga                                                20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 33
ctgattcaag gctttggcag                                                20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: S-ASO

<400> SEQUENCE: 34
ttccccagat gcacctgttt                                                20

<210> SEQ ID NO 35
<211> LENGTH: 58
<212> TYPE: RNA
<213> ORGANISM: Artificial Sequence
<220> FEATURE:
<223> OTHER INFORMATION: Description of Artificial Sequence: Gag mRNA

<400> SEQUENCE: 35
gacuagcgga ggcuagaagg agagagaugg gugcgagagc gucaguauua agcggggg     58

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: S-ASO

<400> SEQUENCE: 36
tcttcctctc tctacccacg ctctc                                          25

<210> SEQ ID NO 37
<211> LENGTH: 25
<212> TYPE: DNA
<213> ORGANISM: Artificial Sequence
```

-continued

<220> FEATURE:
<223> OTHER INFORMATION: Description of Artificial Sequence: S-ASO

<400> SEQUENCE: 37
cctctctcta cccacgctct cgcag    25

<210> SEQ ID NO 38
<211> LENGTH: 296
<212> TYPE: DNA/RNA
<213> ORGANISM: Artificial Sequence
<220> FEATURE:
<223> OTHER INFORMATION: Description of Artificial Sequence: Example
      Sequence

<400> SEQUENCE: 38
cugcagaaau aacuagguac uaagcccguu ugugaaaagu ggccaaaccc auaaauuugg    60
caauuacaau aaagaagcua aaauguggu caaacucaca aacauuuuua uuauauacau    120
uuuaguagcu gaugcuuaua aaagcaauau uuaaaucgua aacaacaaau aaaauaaaau    180
uuaaacgaug ugauuaagag ccaaaggucc ucuagaaaaa gguauuuaag caacggaauu    240
ccuugguguu aguacuauuu uaacgaauaa uaaaaucagg uauagguaac uaaaaa        296